United States Patent
Kley et al.

(10) Patent No.: US 11,433,045 B2
(45) Date of Patent: *Sep. 6, 2022

(54) TREATMENT OF METABOLIC DISORDERS IN CANINE ANIMALS

(71) Applicant: Boehringer Ingelheim Vetmedica GmbH, Ingelheim am Rhein (DE)

(72) Inventors: Saskia Kley, Appenheim (DE); Dania Reiche, Bingen am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/790,810

(22) Filed: Feb. 14, 2020

(65) Prior Publication Data

US 2020/0179328 A1  Jun. 11, 2020

Related U.S. Application Data

(63) Continuation of application No. 15/113,127, filed as application No. PCT/EP2015/050940 on Jan. 20, 2015, now Pat. No. 10,603,300.

(30) Foreign Application Priority Data

Jan. 23, 2014 (EP) .................................. 14152327
Sep. 25, 2014 (EP) .................................. 14186477

(51) Int. Cl.
*A61K 31/351* (2006.01)
*A61P 9/12* (2006.01)
(Continued)

(52) U.S. Cl.
CPC .......... *A61K 31/351* (2013.01); *A61K 9/0053* (2013.01); *A61K 9/02* (2013.01);
(Continued)

(58) Field of Classification Search
CPC combination set(s) only.
See application file for complete search history.

(56) References Cited

U.S. PATENT DOCUMENTS 7,589,193 B2  9/2009 Washburn et al.
7,745,414 B2  6/2010 Eckhardt et al.
(Continued)

FOREIGN PATENT DOCUMENTS

CA  2519584  9/2005
EP  2048150 A1  4/2009
(Continued)

OTHER PUBLICATIONS

Adachi et all., "T-1095, a Renal Na+-Glucose Transporter Inhibitor, Improves Hyperglycemia in Streptozotocin-Induced Diabetic Rats" Metabolism vol. 49 No. 8 pp. 990-995 (Year: 2000).*
(Continued)

*Primary Examiner* — Eric Olson

(57) ABSTRACT

The present invention relates to one or more SGLT2 inhibitors or pharmaceutically acceptable forms thereof for use in the treatment and/or prevention of a metabolic disorder in a canine animal, preferably wherein the metabolic disorder is one or more selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences, such as hypertension, renal dysfunction and/or muscoskeletal disorders, and/or Syndrome X (metabolic syndrome), wherein preferably the development of hyperglycemia induced cataract formation is prevented or remission is achieved and/or wherein preferably the development of metabolic disorder consequences, such as hypertension, renal dysfunction and/or muscoskeletal disorders, is prevented or progression is slowed or remission is achieved.

13 Claims, 4 Drawing Sheets

(51) Int. Cl.

| | | |
|---|---|---|
| *A61P 3/00* | (2006.01) | |
| *A61P 3/10* | (2006.01) | |
| *A61K 38/28* | (2006.01) | |
| *A61K 9/20* | (2006.01) | |
| *A61K 9/48* | (2006.01) | |
| *A61K 9/02* | (2006.01) | |
| *A61K 31/7034* | (2006.01) | |
| *A61K 45/06* | (2006.01) | |
| *A61K 9/08* | (2006.01) | |
| *A61K 31/00* | (2006.01) | |
| *C07D 309/10* | (2006.01) | |
| *A61P 5/50* | (2006.01) | |
| *A61P 27/12* | (2006.01) | |
| *A61K 47/22* | (2006.01) | |
| *A61K 31/352* | (2006.01) | |
| *A61K 9/14* | (2006.01) | |
| *A61P 3/06* | (2006.01) | |
| *C07D 493/08* | (2006.01) | |
| *A61P 3/04* | (2006.01) | |
| *A61P 31/12* | (2006.01) | |
| *A61P 29/00* | (2006.01) | |
| *A61K 9/00* | (2006.01) | |
| *A61K 31/401* | (2006.01) | |

(52) U.S. Cl.
CPC ........... *A61K 9/08* (2013.01); *A61K 9/145* (2013.01); *A61K 9/2009* (2013.01); *A61K 9/2013* (2013.01); *A61K 9/2018* (2013.01); *A61K 9/2027* (2013.01); *A61K 9/2059* (2013.01); *A61K 9/4825* (2013.01); *A61K 9/4858* (2013.01); *A61K 9/4866* (2013.01); *A61K 31/00* (2013.01); *A61K 31/352* (2013.01); *A61K 31/401* (2013.01); *A61K 31/7034* (2013.01); *A61K 38/28* (2013.01); *A61K 45/06* (2013.01); *A61K 47/22* (2013.01); *A61P 3/00* (2018.01); *A61P 3/04* (2018.01); *A61P 3/06* (2018.01); *A61P 3/10* (2018.01); *A61P 5/50* (2018.01); *A61P 9/12* (2018.01); *A61P 27/12* (2018.01); *A61P 29/00* (2018.01); *A61P 31/12* (2018.01); *C07D 309/10* (2013.01); *C07D 493/08* (2013.01)

(56) References Cited

U.S. PATENT DOCUMENTS

| | | | |
|---|---|---|---|
| 7,851,502 B2 | 12/2010 | Bindra et al. | |
| 8,080,580 B2 | 12/2011 | Mascitti et al. | |
| 8,088,743 B2 * | 1/2012 | Washburn | A61K 31/00 514/23 |
| 8,316,972 B2 * | 11/2012 | Hutcheson | B25J 9/08 180/65.1 |
| 8,987,323 B2 | 3/2015 | Cai et al. | |
| 9,145,434 B2 | 9/2015 | Eckhardt et al. | |
| 10,220,017 B2 * | 3/2019 | Weiler | A61P 13/12 |
| 10,603,300 B2 * | 3/2020 | Kley | A61K 9/0053 |
| 2003/0064935 A1 | 4/2003 | Gougoutas | |
| 2007/0259821 A1 | 11/2007 | Eckhardt et al. | |
| 2009/0143316 A1 | 6/2009 | Imamura et al. | |
| 2010/0167988 A1 | 7/2010 | Gant et al. | |
| 2010/0167989 A1 | 7/2010 | Gant et al. | |
| 2010/0249392 A1 | 9/2010 | Eckhardt et al. | |
| 2011/0212905 A1 * | 9/2011 | Nomura | A61P 3/10 514/23 |
| 2012/0237593 A1 | 9/2012 | Comiskey et al. | |
| 2012/0277175 A1 | 11/2012 | Neto et al. | |
| 2013/0046088 A1 * | 2/2013 | Liou | A61P 7/10 536/55 |
| 2014/0031540 A1 | 1/2014 | Eckhardt et al. | |
| 2014/0303096 A1 | 10/2014 | Reiche et al. | |
| 2015/0164856 A1 | 6/2015 | Reiche et al. | |
| 2015/0272977 A1 | 10/2015 | Reiche et al. | |
| 2017/0056366 A1 | 3/2017 | Weiler et al. | |
| 2017/0071969 A1 | 3/2017 | Reiche et al. | |
| 2017/0239281 A1 | 8/2017 | Reiche et al. | |

FOREIGN PATENT DOCUMENTS

| | | | |
|---|---|---|---|
| KR | 1020110118668 | 3/2017 | |
| WO | WO01/27128 * | 4/2001 | ........... C07H 15/203 |
| WO | 2002083066 A2 | 10/2002 | |
| WO | 2004063209 | 7/2004 | |
| WO | 2007077457 A2 | 7/2007 | |
| WO | 2007093610 A1 | 8/2007 | |
| WO | 2007128749 A1 | 11/2007 | |
| WO | 2007129053 A1 | 11/2007 | |
| WO | 2008002824 A1 | 1/2008 | |
| WO | 2008042688 A2 | 4/2008 | |
| WO | 2008116179 A1 | 9/2008 | |
| WO | 2009124755 A1 | 10/2009 | |
| WO | 2009143020 A1 | 11/2009 | |
| WO | 2010022313 | 2/2010 | |
| WO | 2010023594 A1 | 3/2010 | |
| WO | 2010048358 A2 | 4/2010 | |
| WO | 2010092123 | 8/2010 | |
| WO | 2010092125 A1 | 8/2010 | |
| WO | 2010092123 A8 | 6/2011 | |
| WO | 2011117295 A1 | 9/2011 | |
| WO | 2011153712 | 12/2011 | |
| WO | 2012062698 A1 | 5/2012 | |
| WO | 2012140597 A1 | 10/2012 | |
| WO | 2013040164 | 3/2013 | |
| WO | 2014016381 A1 | 1/2014 | |
| WO | 2014068007 | 5/2014 | |
| WO | 2014161836 A1 | 10/2014 | |
| WO | 2015091313 A1 | 6/2015 | |
| WO | 2015110402 A1 | 7/2015 | |
| WO | 2015150299 A2 | 10/2015 | |
| WO | 2016046150 | 3/2016 | |
| WO | 2017032799 A1 | 3/2017 | |

OTHER PUBLICATIONS

Merriam-Webster's Collegiate Dictionary, Tenth Edition, copyright 1998 by Merriam-Webster, Inc, p. 924 (Year: 1998).*

Grempler et al., "Dapagliflozin, a novel selective sodium glucose cotransporter-2 (SGLT-2) inhibitor: characterisation and comparison wih other SGLT2 inhibitors" Diabetes, Obesity, and Metabolism vol. 14 pp. 83-90 (Year: 2012).*

Sako et al., "Time-action profiles of insulin detemir in normal and diabetic dogs" Research In Veterinary Science vol. 90 pp. 396-403 (Year: 2011).*

Deshpande et al., "A Practical Stereoselective Synthesis and Novel Cocrystallizations of an Amphiphatic SGLT-2 Inhibitor". Organic Process Research & Development, vol. 16, 2012, pp. 577-585.

Frank et al., "Equine Metabolic Syndrome", ACVIM Consensus Statement, Journal of Veterinary Internal Medicine, vol. 24, No. 3, 2010, pp. 467-475.

Hirayama et al., Common mechanisms of inhibition for the Na+/glucose (hSGLT1) and Na+/C1-GABA (HGAT1) contransporters). British Journal of Pharmacology, vol. 134, Oct. 2001, pp. 484-495.

International Search Report and Written Opinion for PCT/EP2015/050940 dated Mar. 26, 2015.

Kakinuma et al., "(1S)-1,5-Anhydro-1-[5-(4-ethoxybenzyl)-2-methoxy-4-methylphenyl]-1-thio-d-glucitol (TS-071) is a Potent, Selective Sodium-Dependent Glucose Cotransporter 2 (SGLT2) Inhibitor for Type 2 Diabetes Treatment". Journal of Medicinal Chemistry, vol. 53, No. 8, 2010, pp. 3247-3261.

Osto et al., "Diabetes from humans to cats". General and Comparative Endocrinology, vol. 182, 2013, pp. 48-53.

Rand, Jacquie S., "Pathogenesis of Feline Diabetes". Veterinary Clinics of North America, vol. 43, 2013, pp. 221-231.

Tirmenstein et al., "Nonclinical Toxicology Assessments Support the Chronic Safety of Dapagliflozin, a First-in-Class Sodium-

(56) References Cited

OTHER PUBLICATIONS

Glucose Cotransporter 2 Inhibitor". International Journal of Toxicology, vol. 32, No. 5, 2013, pp. 336-350.
Xu et al., "Design, Synthesis, and Biological Evaluation of Deuterated C-Aryl Glycoside as a Potent and Long-Acting Renal Sodium-Dependent Glucose Cotransporter 2 Inhibitor for the Treatment of Type 2 Diabetes". Journal of Medicinal Chemistry, vol. 57, 2014, pp. 1236-1251.
Johnson et al., "Medical Implications of Obesity in Horses-Lessons for Human Obesity." Journal of Diabetes Science and Technology, vol. 3, No. 1, Jan. 2009, pp. 164-174.
French et al., "Pharmacokinetics and metabolic effects of triamcinolone anetonide and their possible relationships to glucocorticoid-induced laminitis in horses." Journal of Veterinary Pharmacology and Therapeutics, vol. 23, 2000, pp. 287-292.
Treiber et al., "Laminitis in Ponies is a Diabetic-like State" Experimental Biology, The FASEB Journal, Meeting Abstracts, vol. 21, No. 6, Abstract No. 737.23, Apr. 2007, pA833. [Accessed at https://www.fasebj.org/doi/10.1096/fasebj.21.6.A833 on Apr. 17, 2018].
Durham et al., "Type 2 diabetes mellitus with pancreatic b cell dysfunction in 3 horses confirmed with minimal model analysis" Equine Veterinary Journal, vol. 41, No. 9, 2009, pp. 924-929.
Sinha et al., "Pioglitazone-Do we really need it to manage type 2 diabetes?" Diabetes & Metabolic Syndrome: Clnical Research & Reviews, vol. 7, No. 1, 2013, pp. 52-55.
Mahmood, Application of Allometric Principles for the Prediction of Pharmacokinetics in Human and Veterinary Drug Development, Advanced Drug Delivery Reviews 59 (2007), pp. 1177-1192.
Ciobotaru, Emilia, "Diabetes Mellitus—Insights and Perspectives", Editor: Oluwafemi O. Oguntibeju, ISBN 978-953-51-0939-6, Jan. 2, 2013, Chapter 15, Spontaneous Diabetes Mellitus in Animals, pp. 271-296.
Diabetes, vol. 56, Suppl.1, 2007, pp. A144-A145.
Grempler et al., "Empagliflozin, a novel selective sodium glucose cotransporter-2 (SGL T-2) inhibitor Characterisation and comparison with other SGLT-2 inhibitors." Diabetes, Obesity and Metabolism, vol. 14, 2012, pp. 83-90.
Katsuno et al., "Sergliflozin, a Novel Selective Inhibitor of Low-Affinity Sodium Glucose Cotransporter (SGLT2), Validates the Critical Role of SGL T2 in Renal Glucose Reabsorption and Modulates Plasma Glucose Level." The Journal of Pharmacology and Experimental Therapeutics, vol. 320, No. 1, 2007, pp. 323-330.
Sugimoto et al., "Novel Therapeutic Agents for the Treatment of Diabetes Sodium-Glucose Co-Transporter (SGLT) 2 Inhibitors." Cutting-Edge of Medicine, vol. 102, No. 6, 2013, pp. 1474-1483.
Ueta et al., "Reduction of Renal Transport Maximum for Glucose by Inhibition of Na+-Glucose Cotransporter Suppresses Blood Glucose Elevation in Dogs." Biological and Pharmaceutical Bulletin, vol. 29, No. 1, 2006, pp. 114-118.
Yamamoto et al., "TS-071 is a novel, potent and selective renal sodium-glucose cotransporter 2 (SGLT2) inhibitor With anti-hyperglycaemic activity." British Journal of Pharmacology, vol. 164, No. 1, 2011, pp. 181-191.
Iskandar Isris and Richard Donelly; "Sodium-glucose co-transporter-2 inhibitors: an emerging new class of ral antidiabetic drug." Diabetes Obesity and Metabolsm, vol. 11, Issue 2, p. 79-88, Dec. 29, 2008.
Physiological Experiment Guidance, Shi Xueyun, Shanghai Science and Technology Press, published in Jun. 1995, p. 55.
Physiological Experiment Guidance, Shi Xueyun, Shanghai Science and Technology Press, published in Jun. 1995, p. 55 (EN translation).

\* cited by examiner

TREATMENT OF METABOLIC DISORDERS IN CANINE ANIMALS

CROSS-REFERENCE TO RELATED APPLICATIONS

This application is a continuation of U.S. patent application Ser. No. 15/113,127, filed Jul. 21, 2016, which is a national stage of PCT/EP2015/050940, filed Jan. 20, 2015, which claims priority from EP 14152327.4, filed Jan. 23, 2014, and from EP 14186477.7, filed Sep. 25, 2014, the disclosures of which are incorporated herein by reference in their entireties.

FIELD OF THE INVENTION

The present invention relates to veterinary medicine, in particular to the treatment and/or prevention of metabolic disorders in canine animals.

BACKGROUND OF THE INVENTION

Canine animals, e.g. dogs, are affected by various metabolic disorders. A number of metabolic disorders are known in canine animals, including hyperglycaemia, insulin resistance, diabetes, hepatic lipidosis, obesity, hyperinsulinaemia, impaired glucose tolerance, ketosis (in particular ketoacidosis), dyslipidaemia, dysadipokinemia, subclinical inflammation or systemic inflammation, in particular low grade systemic inflammation, which also comprises adipose tissue, Syndrome X (metabolic syndrome) and/or inflammation of the pancreas. Various correlations exist amongst these disorders. Among these disorders, in the dog, diabetes, in particular pre-diabetes and insulin dependent diabetes mellitus, as well as hyperglycaemia, insulin resistance and obesity are gaining more and more importance. This can at least partially be ascribed to changing living and feeding behaviour and that companion animals are living longer due to improved preventive veterinary care during the last years.

Diabetes mellitus is characterized by disturbances in carbohydrate, protein and triglyceride metabolism based on a relative or absolute lack of insulin.

It is a relatively common endocrinopathy in canine animals like the dog. The incidence for diabetes in dogs has increased in the last decades to approximately up to 1.0%. Several risk factors have been identified: age, obesity, neutering, gender and breed.

The current classification divides diabetes mellitus in humans into three classes:
(1.) Type 1 which results from the loss of function of insulin secreting cells, e.g. by immunologic destruction of beta cells or insulin auto-antibodies (juvenile diabetes in humans);
(2.) Type 2 which results from a failure of the insulin stimulated cells to respond properly to insulin stimuli; it is also associated to e.g. amyloid accumulation in beta cells; type 2 usually develops during a long time of the so called pre-diabetes state;
(3.) secondary diabetes mellitus which can due to diabetogenic drugs (e.g. long-acting glucosteroids, megestrol acetat, etc.) or to other primary diseases like pancreatitis, pancreas adenocarcinoma, cushing, hypo- or hyperthyroidism, growth-hormone producing tumors resulting in acromegaly.

Canine diabetes is not easily classified, although there are clear similarities and differences between the human and canine diseases. There is no evidence of a canine equivalent to type 2 diabetes, despite obesity being as much a problem in pet dogs as it is in their owners.

The disease can be broadly divided into insulin deficiency diabetes and insulin resistance diabetes (Catchpole et al., Diabetologia 2005. 48: 1948-1956). Insulin deficiency is the most common type. In contrast to the human situation it is not commonly found in young dogs, but rather has possibly similarities to the latent/late autoimmune diabetes of the adult (LADA) form of type 1 diabetes in man, which is characterised by progressive beta cell destruction by autoimmune reactions.

Autoimmunity in dogs is however controversial. As antibodies have been detected only in a subset of dogs with canine diabetes and are discussed to be a consequence rather than a cause of the disease (Catchpole et al., Diabetologia 2005. 48: 1948-1956).

Additionally, in intact female dogs a dioestrus/gestational dependent insulin resistance diabetes is frequent.

For the treatment of diabetes in humans, especially of type 2 diabetes mellitus, several oral antihyperglycaemic drugs are approved. These drugs act, e.g. by stimulating pancreatic insulin secretion in a glucose-independent or glucose-dependent manner (sulfonylurea/meglitinides, or DPP IV inhibitors, respectively), by enhancing tissue sensitivity to insulin (biguanides, thiazolidinediones), or by slowing postprandial intestinal glucose absorption (alpha-glucosidase inhibitors).

Some oral antihyperglycaemic drugs have been employed, but are either not effective in diabetic dogs e.g. sulfonylurea drugs or did show some effects on glycemic control, but are unfavorable due to high prevalence of adverse effects e.g. alpha-glucosidase inhibitors (Nelson et al. J small Anim Pract 2000, 41, 486-490).

Other approaches have been contemplated for treating diabetes and reduce hyperglycemia, including inhibition of the renal sodium-dependent glucose co-transporter SGLT2. SGLT2 in the kidney regulates glucose levels by mediating the reabsorption of glucose back into the plasma following filtration of the blood. SGLT2 inhibition thus induces glycosuria and may reduce blood glucose levels. For example, compound 1-cyano-2-(4-cyclopropyl-benzyl)-4-(β-D-glucopyranos-1-yl)-benzene is described as an SGLT2 inhibitor in WO 2007/128749. A large variety of further SGLT2 inhibitors are also known. In WO 2011/117295, which is concerned with the medication of predominantly carnivorous non-human animals with dipeptidyl peptidase IV (DPP-IV) inhibitors, various SGLT2 inhibitors are recited amongst numerous other types of compounds in the context of combination therapies with DPP-IV inhibitors.

SGLT2 inhibition has not previously been contemplated for treatment of metabolic disorders in canine animals, such as dogs. In canine animals, medications for metabolic disorders are far less advanced than in humans. Unfortunately, even if a treatment or prophylaxis is effective in humans, e.g., or other non-canine animals, it is not possible to conclude that the same approach will also be effective, safe and otherwise appropriate in a canine animal, such as a dog.

Canine animals differ significantly from humans or, e.g., other carnivores as cats in respect of their metabolisms.

Consequently, the pathophysiology of canine metabolic disorders, and thus also their responses to medication of such disorders differs from other species.

Dogs display obesity and all characteristics of a metabolic syndrome similar to e.g. humans and also cats. In contrast to these species, in canine animals this syndrome does not progress to a type 2 diabetes. A pathophysiological hallmark of type 2 diabetes in humans as well as in felines—the pancreatic islet amyloid deposition is absent in dogs (Verkest, Vet J, in press doi.org/10.1016/j.tvjl.2013.09.057)

Diabetic complication e.g. vision problems are commonly seen with diabetes mellitus in dogs, but are rarely found in feline animals. Though, retinopathy is frequently detected in human diabetics—in dogs it is rarely found, but vision problems arise from keratopathy and especially cataracts. These are encountered in up to 80% of diabetic dogs (Beam et al. Vet. Ophtalmol 1999. 2, 169-172)

Optimal glycaemic control has been shown to be crucial to prevent the development or progression of cataracts (Wang et al. J Diabet. Compl. in press, doi:0.1016/j.jdiacomp.2013.11.002)

The gold-standard treatment of diabetic dogs is currently considered to be injection of insulin. However, no single type of insulin is routinely effective in maintaining control of glycaemia, even with twice-daily administration. Even regulated diabetics may eventually reach a point where their blood glucose is no longer controlled and the insulin must be adjusted, whether by dose or type.

Also with strict compliance from the owner control is often poor and secondary problems are common. Many owners find it impossible to achieve acceptable levels of compliance, as synchronization of food intake and insulin injection is impossible in the majority of cases. Ultimately many dogs with diabetes mellitus are euthanized because of the disease.

The factors governing patient and owner compliance are also very different. In dogs, oral administration, e.g., is yet more highly desirable than in humans.

A treatment that would allow better compliance and therefore better glycaemic control than current insulin-based treatments would help to attenuate the progression of the disease and delay or prevent onset of complications in many animals.

No satisfactory treatment is currently available for metabolic disorders such as obesity, insulin resistance, hyperglycaemia, hyperinsulinaemia, impaired glucose tolerance, hepatic lipidosis, dyslipidaentia, dysadipokinemia, subclinical inflammation or systemic inflammation, in particular low grade systemic inflammation, which also comprises adipose tissue, and associated disorders, such as Syndrome X (metabolic syndrome). Furthermore, these metabolic disorders can be associated to or induced by hypo- or hyperthyroidism, hypercortisolism (hyperadrenocorticism, coshing) and/or growth-hormone access (acromegaly). These metabolic disorders might become clinically manifest e.g. by hypertension, cardiomyopathy, renal dysfunction and/or musculoskeletal disorders in canine animals.

Thus, there remains a particular need for effective, safe and otherwise appropriate treatments of metabolic disorders, including diabetes, in canine animals.

DISCLOSURE OF THE INVENTION

Summary of the Invention

The present inventors have surprisingly found that inhibition of SGLT2 is effective and safe in the treatment and/or prevention of metabolic disorders in canine animals.

The present invention thus provides the use of one or more SGLT2 inhibitors or a pharmaceutically acceptable form thereof in the treatment and/or prevention of a metabolic disorder of a canine animal. Further, the present invention provides the use of one or more SGLT2 inhibitors or a pharmaceutically acceptable form thereof in the treatment and/or prevention of a metabolic disorder of a canine animal, wherein the one or more SGLT2 inhibitors is 1-cyano-2-(4-cyclopropyl-benzyl)-4-(β-D-glucopyranos-1-yl)-benzene (which is referred to in the following as compound A) or a pharmaceutically acceptable form thereof.

Compound A has the following chemical formula:

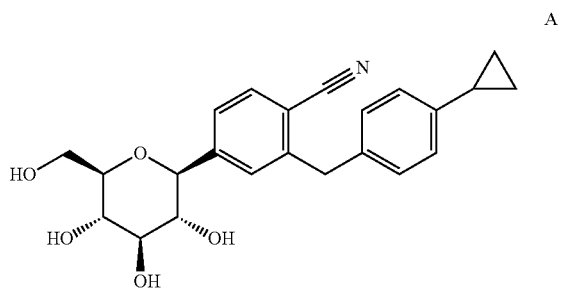 [SMILES: N#Cc1ccc([C@@H]2O[C@H](CO)[C@@H](O)[C@H](O)[C@H]2O)cc1Cc1ccc(C2CC2)cc1]

Further aspects of the invention are defined below as well as in the claims.

The pharmaceutically acceptable form of the one or more SGLT2 inhibitors, preferably compound A, may be a crystalline complex between the one or more SGLT2 inhibitors and one or more amino acids, such as proline.

According to the invention, the one or more SGLT2 inhibitors, preferably compound A, or pharmaceutically acceptable form thereof may be provided, e.g., for oral or parenteral administration, preferably for oral administration.

The one or more SGLT2 inhibitors, preferably compound A, or a pharmaceutically acceptable form thereof may be administered in dosages of 0.1 to 3.0 mg/kg body weight per day, preferably from 0.2 to 2.0 mg/body weight per day, more preferably from 0.1 to 1 mg/body weight per day. Thus, the one or more SGLT2 inhibitors, preferably compound A, or pharmaceutically acceptable form thereof may be prepared for the administration of 0.1 to 3.0 mg/kg body weight per day, preferably from 0.2 to 2.0 mg/kg body weight per day, more preferably from 0.1 to 1 mg/kg body weight per day.

The one or more SGLT2 inhibitors, preferably compound A, or pharmaceutically acceptable form thereof is preferably administered only once per day.

The present invention also provides a pharmaceutical composition comprising one or more SGLT2 inhibitors, preferably compound A, or a pharmaceutically acceptable form thereof, for use according to the invention as disclosed herein.

In the examples provided herein, therapeutic and/or prophylactic benefits resulting from inhibition of SGLT2 according to the present invention are demonstrated experimentally. Experimental data disclosed herein are intended to illustrate the invention, but not to have any limiting effect upon the scope of protection, which is defined herein below by the claims.

In particular, the present inventors have surprisingly found that the use of one or more SGLT2 inhibitors, preferably compound A, according to the present invention advantageously leads to a reduction of hyperglycaemia and/or additionally to an improved e.g. 9 or 24 h glycaemic profile in a hyperglycaemic (e.g. diabetic) canine. Thus, this can result in a reduction of insulin needed to treat diabetic canine animals.

As the absorption and onset of action (glycosuria) is very fast and prominent (Examples 1 and 2) treating a canine with a newly diagnosed metabolic disorder allows to establish the optimal dose in a short time (e.g. 7-14 days).

The invention shows major improvement and optimized treatment of hyperglycaemia and thus allows the possibility of preventing or delaying the progression or inducing a remission of hyperglycaemia associated complications, in particular diabetic cataract formation, in canine animals.

A further advantage of the present invention is that the use of one or more SGLT2 inhibitors, preferably compound A, is effective against the metabolic disorders alone, i.e., if desired the use of one or more SGLT2 inhibitors, preferably compound A, in a canine animal provides a monotherapy, i.e. a stand-alone therapy; i.e., no other medication is administered to the canine animal for the treatment or prevention of the same metabolic disorder—with the only exemption of insulin dependent diabetes.

However, the invention also allows for the possibility of combination therapy with insulin. Such a combination advantageously leads to a decrease in the dose and/or frequency at which the insulin is administered, compared to monotherapy of the canine animal with insulin.

Advantageously, the use of one or more SGLT2 inhibitors, preferably compound A, according to the present invention does not cause hypoglycaemia (Example 2).

A further advantage in particular is that the use of one or more SGLT2 inhibitors, preferably compound A, according to the present invention leads to a reduction in insulin resistance in treated, insulin resistant canine animals. That is, equivalently, the use of one or more SGLT2 inhibitors, preferably compound A, according to the present invention advantageously leads to increased insulin sensitivity in treated, insulin resistant canine animals.

Thus, use of one or more SGLT2 inhibitors, preferably compound A, according to the present invention provides improved treatment and/or prevention of metabolic diseases as disclosed herein, including diabetes, in canine animals.

The effects of using one or more SGLT2 inhibitors, preferably compound A, according to the present invention may be relative to the same or a comparable canine animal prior to administration of one or more SGLT2 inhibitors, preferably compound A according to the present invention, and/or relative to a comparable canine animal that has not received said treatment (e.g. a placebo group). In either case, when a comparison is made, the comparison may be made after a certain treatment period, e.g., 1, 2, 3, 4, 5, 6 or 7 days; 10 days, 14 days; 1, 2, 3, 4, 5, 6, 7 or 8 weeks; 1, 2, 3 or 4 months. Preferably the treatment period is 4 weeks. Alternatively, the treatment period may be 6 or 8 weeks. Alternatively, the treatment period may be 8 weeks or more, e.g. 8-16 weeks, i.e. 8, 9, 10, 11, 12, 13, 14, 15 or 16 weeks.

A further advantage of the present invention is that one or more SGLT2 inhibitors, preferably compound A, may effectively be administered to a canine animal orally. Moreover, the one or more SGLT2 inhibitors, preferably compound A, according to the present invention can be administered only once per day. These advantages allow for better compliance of the treated canine animal and the owner. This leads to better glycaemic control of disorders (e.g. diabetes) for which canine animals are currently treated with insulin. Generally, the use of one or more SGLT2 inhibitors, preferably compound A, according to the present invention thus helps to attenuate (i.e. delays or prevents) the progression of metabolic disorders and delays or prevents the onset of metabolic disorders (e.g. diabetes) and their complications in canine animals.

The effects of using one or more SGLT2 inhibitors, preferably compound A, according to the present invention (e.g. the above-mentioned beneficial effects upon hyperglycaemia) may be relative to the same or a comparable canine animal prior to administration of the one or more SGLT2 inhibitors, preferably compound A, according to the present invention, and/or relative to a comparable canine animal that has received e.g. standard insulin treatment (e.g. a control group) or has been untreated.

A further advantage of the present invention is that the one or more SGLT2 inhibitors, preferably compound A, may effectively be administered to a canine animal orally, e.g. in liquid form. Moreover, the one or more SGLT2 inhibitors, preferably compound A, according to the present invention can be administered only once per day. These advantages allow for optimal dosing and compliance of the treated canine animal and owner.

Accordingly, the present invention also provides pharmaceutical compositions comprising one or more SGLT2 inhibitors, preferably compound A, according to the invention for use in treating and/or preventing metabolic disorders in canine animals.

The invention also provides methods of treating and/or preventing metabolic disorders in canine animals, comprising administering to a canine animal in need of such treatment and/or prevention an effective dose of one or more SGLT2 inhibitors, preferably compound A, as described herein.

Generally, the use of one or more SGLT2 inhibitors, preferably compound A, according to the present invention may thus attenuate, delay or prevent the progression of a metabolic disorder, e.g. the metabolic disorders disclosed herein, or may delay the progression or prevent the onset of metabolic disorders and their complications in canine animals, e.g. hypertension, renal dysfunction and/or musculoskeletal disorders is prevented or progression is slowed or remission is achieved.

Definitions

All values and concentrations presented herein are subject to inherent variations acceptable in biological science within an error of ±10%. The term "about" also refers to this acceptable variation.

Treatment effects disclosed herein (such as an improvement, reduction or delayed onset of a disorder, disease or condition, or the improvement, reduction, increase or delay of any effect, index, marker level or other parameter relating to a disorder, disease or condition) may be observed with a statistical significance of $p<0.05$, preferably $<0.01$.

When reference is made herein to a deviation (e.g. an increase, elevation, excess, prolongation, raise, reduction, decrease, improvement, delay, abnormal levels, or any other change, alteration or deviation with respect to a reference), the deviation may be, e.g., by 5% or more, particularly 10% or more, more particularly 15% or more, more particularly 20% or more, more particularly 30% or more, more particularly 40% or more, or more particularly 50% or more, with respect to the relevant reference value, unless otherwise stated. Typically, the deviation will be by at least 10%, i.e. 10% or more. The deviation may also be by 20%. The deviation may also be by 30%. The deviation may also be by 40%. The relevant reference value may be generated from a group of reference animals which are treated with placebo instead of the one or more SGLT2 inhibitors, preferably compound A, or are untreated.

Herein, an excursion, e.g. an insulin excursions or glucose excursion, designates a change in concentration or level in blood over time. The magnitude of excursions, e.g. insulin excursions or glucose excursions may be expressed as area-under-curve (AUC) values.

Herein, the terms "active substance" or "active ingredient" encompass one or more SGLT2 inhibitors, preferably compound A, or any pharmaceutically acceptable form thereof (e.g. a prodrug or a crystalline form), for use according to the invention. In the case of a combination with one or additional active compound, the terms "active ingredient" or "active substance" may also include the additional active compound.

Herein, the expression "clinical condition(s)" refers to pathologic condition(s) or pathophysiological or physiological changes that are recognizable, e.g. visible and/or measurable, such as blood parameters, and that are associated with and/or define a disorder and/or disease.

Herein, the expression "associated with", in particular encompasses the expression "caused by".

Herein, ivGTT refers to an intravenous glucose tolerance test. In an ivGTT, 0.8 g dextrose per kg body mass may typically be employed.

Herein, ivITT refers to an intravenous insulin tolerance test. In an ivITT, 0.05 U insulin per kg body mass may typically be employed.

SGLT2 Inhibitors

SGLT2 inhibitors for use according to the invention include, but are not limited to, glucopyranosyl-substituted benzene derivatives, for example as described in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940, WO 2009/022020 or WO 2009/022008.

Moreover, the one or more SGLT2 inhibitors for use according to the invention may be selected from the group consisting of the following compounds or pharmaceutically acceptable forms thereof:

(1) a glucopyranosyl-substituted benzene derivative of the formula (1)

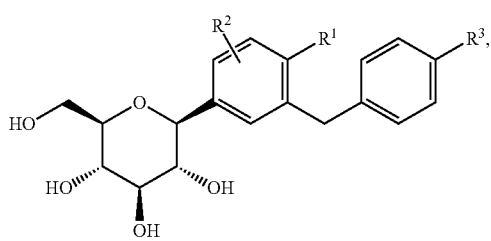

wherein $R^1$ denotes cyano, Cl or methyl (most preferably cyano);

$R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein R3 is preferably selected from cyclopropyl, ethyl, ethinyl, ethoxy, (R)-tetrahydrofuran-3-yloxy or (S)-tetrahydrofuran-3-yloxy; and most preferably R3 is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) 1-cyano-2-(4-cyclopropyl-benzyl)-4-(β-D-glucopyranos-1-yl)-benzene, represented by formula (2):

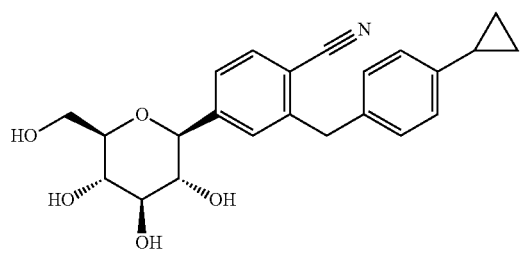 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

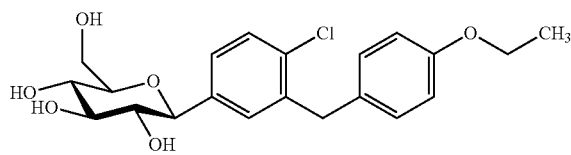

(4) Canagliflozin, represented by formula (4):

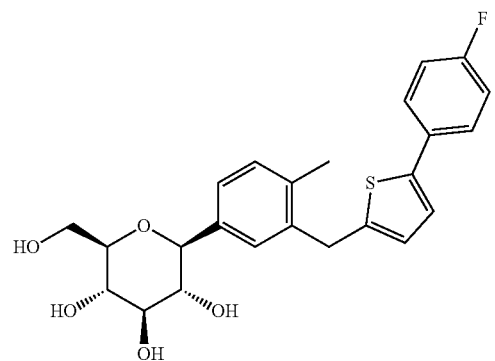 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):

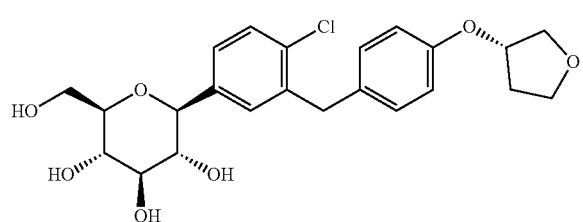 [SMILES: OC[C@H]1O[C@@H](c2ccc(Cl)c(Cc3ccc(O[C@H]4CCOC4)cc3)c2)[C@H](O)[C@@H](O)[C@@H]1O]

(6) Luseogliflozin, represented by formula (6):

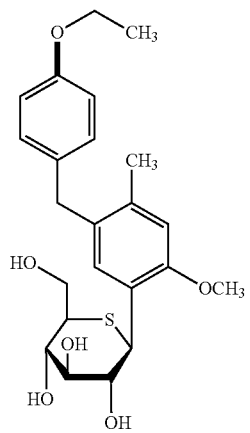

(7) Tofogliflozin, represented by formula (7):

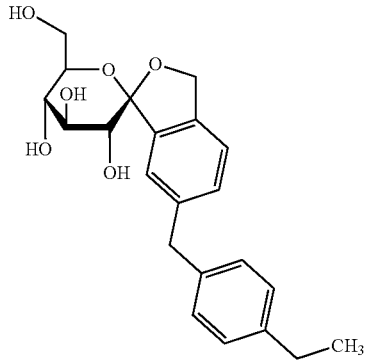

(8) Ipragliflozin, represented by formula (8):

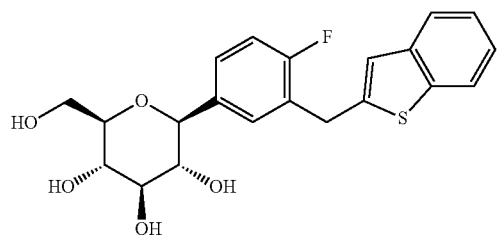 [SMILES: OC[C@H]1O[C@@H](c2ccc(F)c(Cc3cc4ccccc4s3)c2)[C@H](O)[C@@H](O)[C@@H]1O]

(9) Ertugliflozin, represented by formula (9):

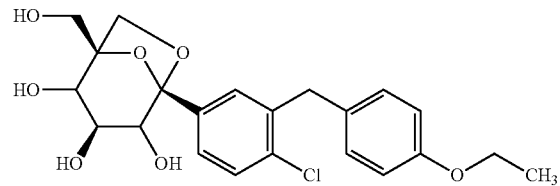 [SMILES: CCOc1ccc(Cc2cc([C@]34OC[C@](CO)(O3)C(O)[C@H](O)C4O)ccc2Cl)cc1]

(10) Atigliflozin, represented by formula (10):

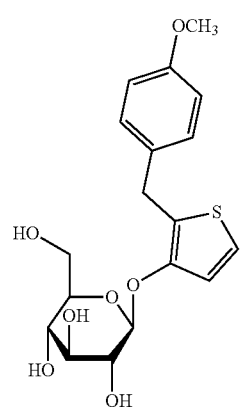

(11) Remogliflozin, represented by formula (11):

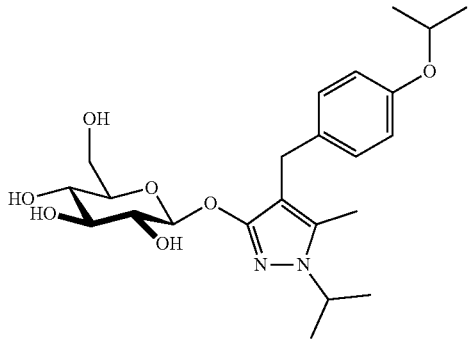

(12) a thiophene derivative of the formula (12)

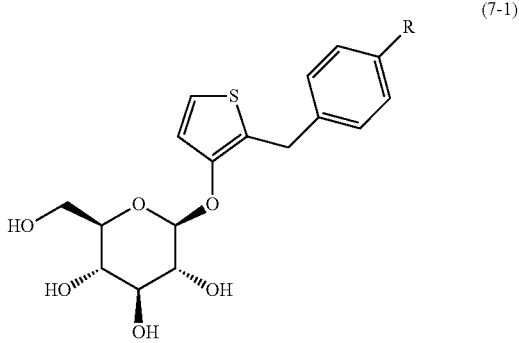

wherein R denotes methoxy or trifluoromethoxy;
(13) 1-β-D-glucopyranosyl)-4-methyl-3-[5-(4-fluorophenyl)-2-thienylmethyl]benzene as described in WO 2005/012326, represented by formula (13);

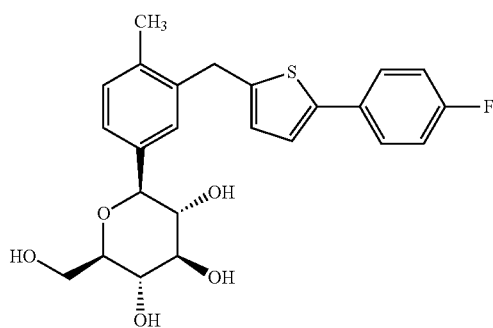 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

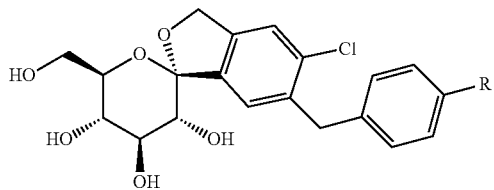

wherein R denotes methoxy, trifluoromethoxy, ethoxy, ethyl, isopropyl or tert. butyl;

(15) a pyrazole-O-glucoside derivative of the formula (15)

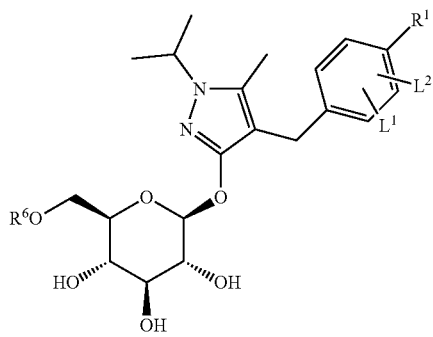

wherein
R$^1$ denotes C$_{1-3}$-alkoxy,
L$^1$, L$^2$ independently of each other denote H or F,
R$^6$ denotes H, (C$_{1-3}$-alkyl)carbonyl, (C$_{1-6}$-alkyl)oxycarbonyl, phenyloxycarbonyl, benzyloxycarbonyl or benzylcarbonyl;

(16) a compound of the formula (16):

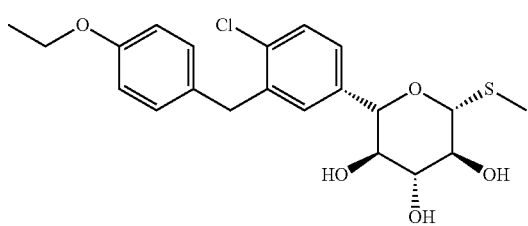

(17) and Sergliflozin, represented by formula (17):

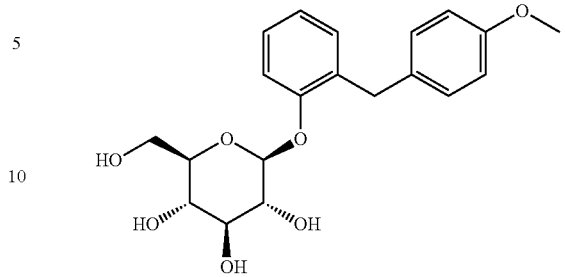

The term "dapagliflozin" as employed herein refers to dapagliflozin of the above structure as well as pharmaceutically acceptable forms thereof, including hydrates and solvates thereof, and crystalline forms thereof. The compound and methods of its synthesis are described in WO 03/099836 for example. Preferred hydrates, solvates and crystalline forms are described in the patent applications WO 2008/116179 and WO 2008/002824 for example.

The term "canagliflozin" as employed herein refers to canagliflozin of the above structure as well as pharmaceutically acceptable forms thereof, including hydrates and solvates thereof, and crystalline forms thereof. The compound and methods of its synthesis are described in WO 2005/012326 and WO 2009/035969 for example. Preferred hydrates, solvates and crystalline forms are described in the patent application WO 2008/069327 for example.

The term "empagliflozin" as employed herein refers to empagliflozin of the above structure as well as pharmaceutically acceptable forms thereof, including hydrates and solvates thereof, and crystalline forms thereof. The compound and methods of its synthesis are described in WO 2005/092877, WO 2006/120208 and WO 2011/039108 for example. A preferred crystalline form is described in the patent applications WO 2006/117359 and WO 2011/039107 for example.

The term "atigliflozin" as employed herein refers to atigliflozin of the above structure as well as pharmaceutically acceptable forms thereof, including hydrates and solvates thereof, and crystalline forms thereof. The compound and methods of its synthesis are described in WO 2004/007517 for example.

The term "ipragliflozin" as employed herein refers to ipragliflozin of the above structure as well as pharmaceutically acceptable forms thereof, including hydrates and solvates thereof, and crystalline forms thereof. The compound and methods of its synthesis are described in WO 2004/080990, WO 2005/012326 and WO 2007/114475 for example.

The term "tofogliflozin" as employed herein refers to tofogliflozin of the above structure as well as pharmaceutically acceptable forms thereof, including hydrates and solvates thereof, and crystalline forms thereof. The compound and methods of its synthesis are described in WO 2007/140191 and WO 2008/013280 for example.

The term "luseogliflozin" as employed herein refers to luseogliflozin of the above structure as well as pharmaceutically acceptable forms thereof, including hydrates and solvates thereof, and crystalline forms thereof.

The term "ertugliflozin" as employed herein refers to ertugliflozin of the above structure as well as pharmaceutically acceptable forms thereof, including hydrates and solvates thereof, and crystalline forms thereof. The compound is described for example in WO 2010/023594.

The term "remogliflozin" as employed herein refers to remogliflozin of the above structure as well as pharmaceutically acceptable forms thereof, including prodrugs of remogliflozin, in particular remogliflozin etabonate, including hydrates and solvates thereof, and crystalline forms thereof. Methods of its synthesis are described in the patent applications EP 1 213 296 and EP 1 354 888 for example.

The term "sergliflozin" as employed herein refers to sergliflozin of the above structure as well as pharmaceutically acceptable forms thereof, including prodrugs of sergliflozin, in particular sergliflozin etabonate, including hydrates and solvates thereof, and crystalline forms thereof. Methods for its manufacture are described in the patent applications EP 1 344 780 and EP 1 489 089 for example.

The compound of formula (16) above and its manufacture are described for example in WO 2008/042688 or WO 2009/014970.

Preferred SGLT2 inhibitors are glucopyranosyl-substituted benzene derivatives. Optionally, one or more hydroxyl groups of the glucopyranosyl group in such one or more SGLT2 inhibitors may be acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

More preferred are glucopyranosyl-substituted benzonitrile derivatives of formula (1) as disclosed herein above. Yet more preferred are glucopyranosyl-substituted benzonitrile derivatives of formula (18):

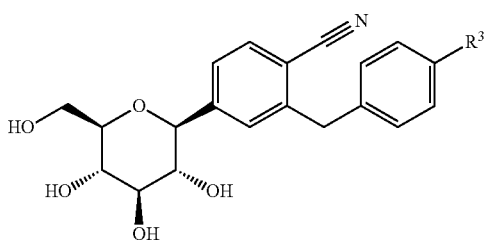

wherein

R3 denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano (wherein R3 is preferably selected from cyclopropyl, ethyl, ethinyl, ethoxy, (R)-tetrahydrofuran-3-yloxy or (S)-tetrahydrofuran-3-yloxy; and R3 most preferably is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

Preferably, such SGLT2 inhibitor is 1-cyano-2-(4-cyclopropyl-benzyl)-4-(β-D-glucopyranos-1-yl)-benzene as shown in formula (2) (also referred to herein as "compound A"). Optionally, one or more hydroxyl groups of the β-D-glucopyranosyl group of compound A may be acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

Thus, in preferred embodiments, a SGLT2 inhibitor according to the present invention is a glucopyranosyl-substituted benzene derivative SGLT2 inhibitor, preferably a SGLT2 inhibitor of formula (1), more preferably of formula (18), or yet more preferably of formula (2) (i.e. compound A), in each case as defined herein above.

Metabolic Disorders

The metabolic disorder may be diabetes, pre-diabetes, obesity and/or any disorder, disease, condition or symptom associated with one or more of those disorders. In particular, the metabolic disorder may be hyperglycaemia, impaired glucose tolerance, insulin resistance, insulin dependent diabetes and/or hepatic lipidosis. Further relevant metabolic disorders include hyperinsulinaemia, impaired glucose tolerance, ketosis (in particular ketoacidosis), hyperlipidaemia, dyslipidemia, elevated blood levels of fatty acids and/or of glycerol, Syndrome X (metabolic syndrome), and/or inflammation of the pancreas, low grade systemic inflammation, inflammation of adipose tissue.

In some embodiments, the metabolic disorder is diabetes. Herein, diabetes may be pre-diabetes, insulin dependent diabetes or insulin resistance diabetes. In particular, diabetes may be insulin dependent diabetes.

In some embodiments, the metabolic disorder is hyperglycaemia. Herein, hyperglycaemia may be associated with diabetes, e.g. with insulin dependent diabetes or insulin resistance diabetes. In some embodiments, hyperglycaemia may be associated with obesity. The hyperglycaemia may be chronic.

In some embodiments, the metabolic disorder is insulin resistance. Herein, insulin resistance may be associated with diabetes, e.g. with insulin resistance diabetes. In some embodiments, insulin resistance may be associated with obesity.

In some embodiments, the metabolic disorder is impaired glucose tolerance (IGT). Herein, impaired glucose tolerance may be associated with diabetes, e.g. with insulin dependent diabetes or insulin resistance diabetes.

In some embodiments, impaired glucose tolerance may be associated with obesity.

In some embodiments, the metabolic disorder is hyperinsulinaemia. Herein, hyperinsulinaemia may be associated with diabetes, e.g. with insulin resistance diabetes. In some embodiments, hyperinsulinaemia may be associated with obesity.

In some embodiments, the metabolic disorder is one or more of hyperglycaemia, insulin resistance, and hepatic lipidosis. In some embodiments, the metabolic disorder is selected from hyperglycaemia and insulin resistance.

In some embodiments, the metabolic disorder is one or more of hyperinsulinaemia, impaired glucose tolerance, hyperglycaemia and insulin resistance.

In certain embodiments, the canine animal is obese. For example, according to the invention, one or more metabolic disorders selected from hyperglycaemia, insulin resistance and hepatic lipidosis may be treated and/or prevented in an obese canine animal. Moreover, e.g., hyperinsulinaemia and/or impaired glucose tolerance may be treated and/or prevented in an obese canine animal. Moreover, one or more disorders selected from ketosis (in particular ketoacidosis), hyperlipidaemia, elevated blood levels of fatty acids and/or of glycerol, Syndrome X (metabolic syndrome), inflammation of the pancreas, inflammation of adipose tissue, may be treated and/or prevented in an obese canine animal.

In certain embodiments, the canine animal is not obese. The metabolic disorder may be associated and/or caused by e.g. hypo- or hyperthyroidism, hypercortisolism (hyperadrenocorticism, cushing) and/or growth-hormone access (acromegaly). For example, according to the invention, one or more metabolic disorders selected from hyperglycaemia, insulin resistance and hepatic lipidosis may be treated and/or prevented in a non-obese canine animal. Moreover, e.g., hyperinsulinaemia and/or impaired glucose tolerance may be treated and/or prevented in a non-obese canine animal. Moreover, one or more disorders selected from ketosis (in particular ketoacidosis), hyperlipidaemia, elevated blood levels of fatty acids and/or of glycerol, Syndrome X (metabolic syndrome), inflammation of the pancreas and/or inflammation of adipose tissue may be treated and/or prevented in a non-obese canine animal.

In certain embodiments, the canine animal is suffering from diabetes, e.g. from insulin dependent diabetes or insulin resistance diabetes. For example, according to the invention, one or more metabolic disorders selected from the group of hyperglycaemia, impaired glucose tolerance and hepatic lipidosis may be treated and/or prevented in a canine animal that is suffering from diabetes, e.g. from insulin dependent diabetes or insulin resistance diabetes. Moreover, e.g., hyperinsulinaemia and/or insulin resistance may be treated and/or prevented in a canine animal that is suffering from diabetes, e.g. from or insulin resistance diabetes. Moreover, one or more disorders selected from ketosis (in particular ketoacidosis), hyperlipidaemia, elevated blood levels of fatty acids and/or of glycerol, Syndrome X (metabolic syndrome), inflammation of the pancreas, inflammation of adipose tissue may be treated and/or prevented in a canine animal that is suffering from diabetes, e.g. from insulin dependent diabetes or insulin resistance diabetes.

In some embodiments, the canine animal is obese and not suffering from diabetes.

In some embodiments, the canine animal is not obese and suffering from diabetes.

The present invention also provides the use of one or more SGLT2 inhibitors, preferably compound A, for treating and/or preventing hyperglycaemia associated complications. For example by improving the diurnal glycaemic control and thereby delay or prevent the development or the progression or induce the regression of cataract formation in a canine animal.

Ketosis is a state of elevated levels of ketone bodies in the body. Ketoacidosis can be described as a type of metabolic acidosis which is caused by high concentrations of ketone bodies, formed by the breakdown of fatty acids and the deamination of amino acids. The two common ketones produced in humans are acetoacetic acid and β-hydroxybutyrate. In dogs, predominantly three ketones are found: acetoacetic acid, beta-hydroxybutyrate and pyruvic acid. Ketoacidosis can be smelled on a subject's breath. This is due to acetone, a direct byproduct of the spontaneous decomposition of acetoacetic acid.

Ketoacidosis is an extreme and uncontrolled form of ketosis. Ketosis is also a normal response to prolonged fasting. In ketoacidosis, the body fails to adequately regulate ketone production, esp. by producing Acetyl-CoA, causing such a severe accumulation of keto acids that the pH of the blood is substantially decreased, i.e. the excess ketone bodies may significantly acidify the blood. In extreme cases ketoacidosis can be fatal.

Ketoacidosis may occur when the body is producing high levels of ketone bodies via the metabolism of fatty acids (ketosis) and insulin does not sufficiently slow this production (e.g. due to insulin resistance/reduced insulin sensitivity or lack of insulin). The presence of high blood sugar levels (hyperglycaemia) caused by the lack of insulin can lead to further acidity in the blood. In healthy individuals this normally does not occur because the pancreas produces insulin in response to rising ketone/blood sugar levels.

Ketoacidosis is most common in untreated diabetes mellitus, when the liver breaks down fat and proteins in response to a perceived need for respiratory substrate.

Pre-diabetes in canine animals is characterized by hyperinsulinemia, insulin resistance in target organs, impaired glucose tolerance incl. e.g. an altered insulin response to a glycaemic challenge, e.g. also e.g. induced by stress. Pre-diabetes is also often associated with obesity. Pre-diabetes may also be associated with intermittent hyperglycaemia.

Insulin resistance diabetes in canine animals is characterized by both increased insulin production and insulin resistance in target organs and as a consequence hyperglycaemia. It is frequently detected in intact female diabetic canines and mainly attributed to progesterone acting as an endogenous insulin antagonist. Therefore, it is mostly either associated with the menstrual cycle, i.e. the dioestrus or to pregnancy—gestational. Genetic factors, glucosteroids, lack of exercise, and obesity are possible further reasons for insulin resistance.

Clinical signs of diabetes mellitus observed with canine animals include polydipsia, polyuria, weight loss, and/or polyphagia. In contrast, in other species such as cats anorexia is more often described than polyphagia. Further particularly relevant clinical signs of diabetes mellitus in canine animals within the context of the present invention are hyperglycaemia and glycosuria. Hyperglycaemia in a canine animal (e.g. a dog) is defined as plasma glucose values above normal values (3.5-7 mmol/l or 60-120 mg/dl), e.g. 8 mmol/l or more or 150 mg/dl or more plasma glucose. Glycosuria in a canine animal (e.g. a dog) is defined as glucose levels in urine above normal values (0~2 mmol/L, or 36 mg/dl). The renal threshold is reached with blood glucose concentrations of approximately 8-11 mmol/l or 150 to 200 mg/dl.

The diagnosis of diabetes mellitus in canine animals may alternatively be based on three criteria, e.g., as follows:
(1) Fasting blood glucose concentration measurements>250 mg/dl;
(2) Glycosuria as defined above; and
(3) One or more of the following: polyuria, polydipsia, polyphagia, weight loss despite good appetite, or ketonuria (without signs of severe ketoacidosis).

In addition to the above mentioned diagnostics and in order to support them, further examinations can include haematology, blood chemistry, x-ray and/or abdominal ultrasound.

Preferably, the use of the one or more SGLT2 inhibitors, preferably compound A, according to the invention allows normal or near-normal blood glucose concentrations to be maintained and/or established. However,—unlike for human therapy—this not believed to be always necessary for diabetic animals and therefore not always the goal of a treatment according to the invention. According to the invention, blood glucose concentrations may also be maintained, e.g., between 5.5 and 16.6 mmol/l or 100 to 300 mg/dl. For canine animals this will often be satisfactory.

Hyperglycaemia induces cataracts are generally acute in onset, rapidly progressive, and bilaterally symmetrical. The clouding of the lens inside the eye leads to a decrease or ultimately loss of vision.

Insulin resistance can be described as the condition in which normal amounts of insulin are inadequate to produce a normal insulin response from fat, muscle and liver cells. Insulin resistance in fat cells reduces the effects of insulin and results in elevated hydrolysis of stored triglycerides in the absence of measures which either increase insulin sensitivity or which provide additional insulin. Increased mobilization of stored lipids in these cells elevates free fatty acids in the blood plasma. Insulin resistance in muscle cells reduces glucose uptake (and so local storage of glucose as glycogen), whereas insulin resistance in liver cells results in impaired glycogen synthesis and a failure to suppress glucose production. Elevated blood fatty acid levels, reduced muscle glucose uptake, and increased liver glucose production, may all contribute to elevated blood glucose levels (hyperglycaemia). In obese dogs insulin resistance, i.e. a 5-fold lower insulin sensitivity than in lean dogs is detected.

Insulin resistance may be present in association with obesity, visceral adiposity, hypertension and dyslipidaemia involving elevated triglycerides, small dense low-density lipoprotein (sdLDL) particles, and decreased HDL cholesterol levels. With respect to visceral adiposity, a great deal of evidence in humans suggests two strong links with insulin resistance. First, unlike subcutaneous adipose tissue, visceral adipose cells produce significant amounts of proinflammatory cytokines such as tumour necrosis factor-alpha (TNF-alpha), and Interleukins-1 and -6, etc. In numerous experimental models, these proinflammatory cytokines profoundly disrupt normal insulin action in fat and muscle cells, and may be a major factor in causing the whole-body insulin resistance observed in human patients with visceral adiposity. Similarly, in canines excessive fat depots contribute to low grade systemic inflammation. The cause of the vast majority of cases of insulin resistance remains unknown. There is clearly an inherited component. However, there are some grounds for suspecting that insulin resistance is related to a high-carbohydrate diet. Inflammation also seems to be implicated in causing insulin resistance.

Hyperinsulinaemia can be described as a condition in which there are excess levels, i.e. more than about 35 pmol/L under basal or about 200 pmol/L during e.g. a glycaemic challenge (e.g. ivGTT or stress) of insulin circulating in the blood. As mentioned, it is commonly present in cases of, and may be a consequence of, insulin resistance in canine animals.

Impaired glucose tolerance can be described as condition in which the response to a after a glycaemic challenge e.g. after a meal or after a loading test (glucose tolerance test) or after stress induced elevation of blood glucose concentration, the glycaemic peak of the glucose excursion is higher and/or the duration of the glucose excursion is prolonged.

Dyslipidaemia or hyperlipidaemia is the presence of raised or abnormal levels of lipids and/or lipoproteins in the blood. Lipid and lipoprotein abnormalities are regarded as a highly modifiable risk factor for cardiovascular disease due to the influence of cholesterol. Glycerol is a precursor for the synthesis of triacylglycerols (triglycerids) and of phospholipids in the liver and adipose tissue. When the body uses stored fat as a source of energy, glycerol and fatty acids are released into the bloodstream after hydrolysis of the triglycerides. The glycerol component can be converted to glucose by the liver and provides energy for cellular metabolism. Normal levels of free fatty acids in the blood of companion (such as canine) animals are triglyceride concentrations of 50 to 150 mg/dl. Normal levels of blood cholesterol are, e.g., 130 to 300 mg/dl for the dog.

Dysadipokinemia can be described as a condition in which the circulating plasma levels of biologically active substances produced in adipose tissue that act in an autocrine/paracrine or endocrine fashion is deviated, e.g. an elevation of leptin and/or a reduction of adiponectin.

Subclinical inflammation or systemic inflammation, in particular low grade systemic inflammation is characterized by increased expression and secretion of pro-inflammatory cytokines such as tumour necrosis factor-alpha and/or lower expression and secretion of anti-inflammatory cytokines e.g. interleukin-10 and/or their respective receptors.

Obesity can be described as a medical condition in which excess body fat has accumulated to the extent that it may have an adverse effect on health, leading to reduced life expectancy. In obese canine, e.g. a body condition score (BCS) of larger than 7 (out of 9) is encountered.

Metabolic disorders to be treated and/or prevented according to the invention include Syndrome X (metabolic syndrome). This disorder can be described as a combination of medical disorders that increase the risk of developing manifest clinical consequences—e.g. hypertension, cardiomyopathy, renal dysfunction and/or musculoskeletal disorders in canine animals.

Metabolic syndrome is also known as metabolic Syndrome X (metabolic syndrome), Syndrome X (metabolic syndrome), insulin resistance syndrome, Reaven's syndrome, and CHAOS (as an abbreviation for Coronary artery disease, Hypertension, Atherosclerosis, Obesity, and Stroke).

The exact mechanisms of the complex pathways of metabolic syndrome are not yet completely known. The pathophysiology is extremely complex and has been only partially elucidated. Most patients are older, obese, sedentary, and have a degree of insulin resistance. The most important factors in order are: (1) overweight and obesity, (2) genetics, (3) aging, and (4) sedentary lifestyle, i.e., low physical activity and excess caloric intake.

The pathophysiology is commonly characterized by the development of visceral fat after which the adipocytes (fat cells) of the visceral fat increase plasma levels of TNF-alpha and alter levels of a number of other substances (e.g., adiponectin, resistin, PAI-1). TNF-alpha has been shown not only to cause the production of inflammatory cytokines, but possibly to trigger cell signalling by interaction with a TNF-alpha receptor that may lead to insulin resistance.

Current first line treatment is change of lifestyle (i.e., caloric restriction and physical activity). However, drug treatment is frequently required. Accordingly, the present invention also provides for prevention of clinically relevant consequences of the metabolic disorder e.g. hypertension, cardiomyopathy, renal dysfunction and for musculoskeletal disorders in canine animals.

Metabolic disorders to be treated and/or prevented according to the invention include inflammation of the pancreas (pancreatitis). This disorder may occur as either an acute form or a chronic form. Chronic pancreatitis may occur with or without steatorrhea and/or diabetes mellitus.

Pancreatitis may be caused by hypertriglyceridemia (in particular when triglyceride values exceed 1500 mg/dl (16 mmol/l), hypercalcemia, viral infection, trauma, vasculitis (i.e. inflammation of the small blood vessels within the pancreas), and autoimmune pancreatitis.

Metabolic disorders, esp. dyslipidaemia and elevated serum levels of triglycerides are risk factors for the development of pancreatitis, and may thus be treated according to the present invention in association with pancreatitis. Accordingly, the present invention also provides for prevention of pancreatitis.

Metabolic disorders to be treated and/or prevented according to the invention include an inflammation of adipose tissue (panniculitis), which is a group of disorders characterised by inflammation of subcutaneous adipose tissue.

Panniculitis may occur in any fatty tissue (cutaneous and/or visceral). It may be diagnosed on the basis of a deep skin biopsy, and can be further classified by histological characteristics based on the location of the inflammatory cells (within fatty lobules or in the septa which separate them) and on the presence or absence of vasculitis. Panniculitis can also be classified based on the presence or absence of systemic symptoms.

Metabolic diseases, esp. pancreatitis, are risk factors for the development of panniculitis, and may thus be treated according to the present invention in association with panniculitis. Accordingly, the present invention also provides for prevention of panniculitis.

Canine Animals

Herein, a canine animal may be a member of the Canidae family (i.e. a canid). It may thus belong either to the subfamily Canini (related to wolves) or Vulpini (related to foxes). The term canine animal encompasses the term dog, e.g., a domestic dog. The term domestic dog encompasses the terms Canis lupus familiaris and Canis lupus dingo.

Pharmaceutically Acceptable Forms

Herein, references to SGLT2 inhibitors and/or their use according to the invention encompass pharmaceutically acceptable forms of the SGLT2 inhibitors, unless otherwise stated.

According to the invention, any pharmaceutically acceptable form of the SGLT2 inhibitor, e.g. of formula (1), preferably formula (18), more preferably formula (2), may be used. E.g. a crystalline form may be used. Prodrug forms are also encompassed by the present invention.

Prodrug forms may include, e.g., esters and/or hydrates. The term prodrug is also meant to include any covalently bonded carrier which releases the active compound of the invention in vivo when the prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention.

Crystalline forms for use according to the invention include a complex of an SGLT2 inhibitor with one or more amino acids (see e.g. WO 2014/016381). An amino acid for such use may be a natural amino acid. The amino acid may be a proteogenic amino acid (including L-hydroxyproline), or a non-proteogenic amino acid. The amino acid may be a D- or an L-amino acid. In some preferred embodiments the amino acid is proline (L-proline and/or D-proline, preferably L-proline). E.g., a crystalline complex of 1-cyano-2-(4-cyclopropyl-benzyl)-4-(β-D-glucopyranos-1-yl)-benzene (formula (2); compound A) with proline (e.g. L-proline) is preferred.

Thus, herein is disclosed a crystalline complex between one or more natural amino acids and an SGLT2 inhibitor, e.g., a crystalline complex between one or more natural amino acids and a glucopyranosyl-substituted benzene derivative SGLT2 inhibitor, preferably a SGLT2 inhibitor of formula (1), more preferably of formula (18) or yet more preferably of formula (2) (compound A). Thus, herein is disclosed a crystalline complex between one or more natural amino acids and 1-cyano-2-(4-cyclopropyl-benzyl)-4-(β-D-glucopyranos-1-yl)-benzene (compound A).

Further disclosed herein is the use of one or more crystalline complexes as defined hereinbefore or hereinafter for preparing a pharmaceutical composition which is suitable for the treatment or prevention of diseases or conditions which can be influenced by inhibiting sodium-dependent glucose co-transporter SGLT, preferably SGLT2. Further disclosed herein is the use of one or more crystalline complexes as defined hereinbefore or hereinafter for preparing a pharmaceutical composition for inhibiting the sodium-dependent glucose co-transporter SGLT2.

A crystalline complex between one or more natural amino acids (e.g. proline, preferably L-proline) and an SGLT2 inhibitor, is a preferred pharmaceutically acceptable form of a SGLT2 inhibitor for use according to the present invention. In particular, a crystalline complex between one or more natural amino acids (e.g. proline, preferably L-proline) and a glucopyranosyl-substituted benzene derivative SGLT2 inhibitor, preferably a SGLT2 inhibitor of formula (1), more preferably of formula (18) or yet more preferably of formula (2) (compound A) is a preferred pharmaceutically acceptable form of a SGLT2 inhibitor for use according to the present invention. A crystalline complex between one or more natural amino acids (e.g. proline, preferably L-proline) and 1-cyano-2-(4-cyclopropyl-benzyl)-4-(β-D-glucopyranos-1-yl)-benzene (compound A) is particularly preferred as a pharmaceutically acceptable form of a SGLT2 inhibitor for use according to the present invention.

Also disclosed herein is a method for making one or more crystalline complexes as defined hereinbefore and hereinafter, said method comprising the following steps:
(a) preparing a solution of the SGLT2 inhibitor (e.g. a glucopyranosyl-substituted benzene derivative, or a SGLT2 inhibitor of formula (1), preferably formula (18) or more preferably formula (2), i.e. compound A) and the one or more natural amino acids in a solvent or a mixture of solvents;
(b) storing the solution to precipitate the crystalline complex out of solution;
(c) removing the precipitate from the solution; and
(d) drying the precipitate optionally until any excess of said solvent or mixture of solvents has been removed.

A certain pharmaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronising) has to be avoided as far as possible, in spite of the hard conditions required during the process, it is essential that the active substance should be highly stable throughout the grinding process. Only if the active substance is sufficiently stable during the grinding process it is possible to produce a homogeneous pharmaceutical formulation which always contains the specified amount of active substance in a reproducible manner.

Another problem which may arise in the grinding process for preparing the desired pharmaceutical formulation is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. Preferably, therefore, a pharmaceutically active substance should be at best slightly hygroscopic.

Furthermore, the availability of a well-defined crystalline form allows the purification of the drug substance by recrystallization.

Apart from the requirements indicated above, it should be generally borne in mind that any change to the solid state of a pharmaceutical composition which is capable of improving its physical and chemical stability gives a significant advantage over less stable forms of the same medicament.

A crystalline complex between a natural amino acid and an SGLT2 inhibitor (e.g. a glucopyranosyl-substituted benzene derivative or a SGLT2 inhibitor of formula (1), or formula (18) or, particularly, of formula (2), i.e. compound A) fulfills important requirements mentioned hereinbefore.

Preferably the natural amino acid is present in either its (D) or (L) enantiomeric form, most preferably as the (L) enantiomer.

Furthermore those crystalline complexes according to this invention are preferred which are formed between the SGLT2 inhibitor (e.g. of formula (1), preferably formula (18) or, particularly, of formula (2), i.e. compound A) and one natural amino acid, most preferably between the compound A and the (L) enantiomer of a natural amino acid.

Preferred amino acids according to this invention are selected from the group consisting of phenylalanine and proline, in particular (L)-proline and (L)-phenylalanine According to a preferred embodiment the crystalline complex is characterized in that the natural amino acid is proline, in particular (L)-proline.

Preferably the molar ratio of the SGLT2 inhibitor (e.g. of formula (1), preferably formula (18) or, particularly, of formula (2), i.e. compound A) and the natural amino acid is in the range from about 2:1 to about 1:3; more preferably from about 1.5:1 to about 1:1.5, even more preferably from about 1.2:1 to about 1:1.2, most preferably about 1:1. In the following such an embodiment is referred to as "complex (1:1)" or "1:1 complex".

Therefore a preferred crystalline complex according to this invention is a complex (1:1) between said SGLT2 inhibitor (e.g. of formula (1), preferably formula (18) or, particularly, of formula (2), i.e. compound A) and proline; in particular of said SGLT2 inhibitor and L-proline.

According to a preferred embodiment the crystalline complex, in the particular the 1:1 complex of said SGLT2 inhibitor with L-proline, is a hydrate.

Preferably the molar ratio of the crystalline complex and water is in the range from about 1:0 to 1:3; more preferably from about 1:0 to 1:2, even more preferably from about 1:0.5 to 1:1.5, most preferably about 1:0.8 to 1:1.2, in particular about 1:1.

The crystalline complex of said SGLT2 inhibitor with proline, in particular with L-proline and water, may be identified and distinguished from other crystalline forms by means of their characteristic X-ray powder diffraction (XRPD) patterns.

For example, a crystalline complex of compound A with L-proline is preferably characterised by an X-ray powder diffraction pattern that comprises peaks at 20.28, 21.14 and 21.64 degrees 2Θ (±0.1 degrees 2Θ), wherein said X-ray powder diffraction pattern is made using $CuK_{\alpha 1}$ radiation.

In particular said X-ray powder diffraction pattern comprises peaks at 4.99, 20.28, 21.14, 21.64 and 23.23 degrees 2Θ (±0.1 degrees 2Θ), wherein said X-ray powder diffraction pattern is made using $CuK_{\alpha 1}$ radiation.

More specifically said X-ray powder diffraction pattern comprises peaks at 4.99, 17.61, 17.77, 20.28, 21.14, 21.64, 23.23 and 27.66 degrees 2Θ (±0.1 degrees 2Θ), wherein said X-ray powder diffraction pattern is made using $CuK_{\alpha 1}$ radiation Even more specifically said X-ray powder diffraction pattern comprises peaks at 4.99, 15.12, 17.61, 17.77, 18.17, 20.28, 21.14, 21.64, 23.23 and 27.66 degrees 2Θ (±0.1 degrees 2Θ), wherein said X-ray powder diffraction pattern is made using $CuK_{\alpha 1}$ radiation.

Even more specifically, the crystalline complex of compound A and L-proline is characterised by an X-ray powder diffraction pattern, made using $CuK_{\alpha 1}$ radiation, which comprises peaks at degrees 2Θ (±0.1 degrees 2Θ) as contained in Table 1.

TABLE 1

X-ray powder diffraction pattern of the crystalline complex of compound A and L-proline (only peaks up to 30° in 2 Θ are listed):

| 2 Θ [°] | d-value [Å] | Intensity $I/I_0$ [%] |
|---|---|---|
| 4.99 | 17.68 | 39 |
| 7.01 | 12.61 | 6 |
| 8.25 | 10.70 | 11 |
| 9.95 | 8.88 | 12 |
| 13.15 | 6.73 | 30 |

TABLE 1-continued

X-ray powder diffraction pattern of the crystalline complex of compound A and L-proline (only peaks up to 30° in 2 Θ are listed):

| 2 Θ [°] | d-value [Å] | Intensity I/I₀ [%] |
|---|---|---|
| 13.33 | 6.64 | 10 |
| 14.08 | 6.28 | 4 |
| 15.12 | 5.85 | 32 |
| 16.40 | 5.40 | 12 |
| 16.49 | 5.37 | 13 |
| 17.11 | 5.18 | 6 |
| 17.61 | 5.03 | 32 |
| 17.77 | 4.99 | 35 |
| 18.17 | 4.88 | 32 |
| 18.32 | 4.84 | 28 |
| 18.72 | 4.74 | 8 |
| 19.16 | 4.63 | 30 |
| 19.96 | 4.45 | 26 |
| 20.28 | 4.37 | 56 |
| 20.60 | 4.31 | 7 |
| 21.14 | 4.20 | 84 |
| 21.64 | 4.10 | 100 |
| 22.33 | 3.98 | 15 |
| 23.23 | 3.83 | 41 |
| 24.06 | 3.70 | 4 |
| 24.51 | 3.63 | 15 |
| 24.93 | 3.57 | 26 |
| 25.89 | 3.44 | 23 |
| 26.21 | 3.40 | 11 |
| 26.84 | 3.32 | 8 |
| 27.66 | 3.22 | 38 |
| 27.96 | 3.19 | 9 |
| 28.26 | 3.16 | 5 |
| 28.44 | 3.14 | 6 |
| 28.75 | 3.10 | 6 |
| 29.18 | 3.06 | 19 |

Even more specifically, said crystalline complex is characterised by an X-ray powder diffraction pattern, made using CuK$_{α1}$ radiation, which comprises peaks at degrees 2Θ (±0.1 degrees 2Θ as shown in FIG. 3.

Furthermore said crystalline complex of the compound A with L-proline is characterized by a melting point of above 89° C., in particular in a range from about 89° C. to about 115° C., more preferably in a range from about 89° C. to about 110° C. (determined via DSC; evaluated as onset-temperature; heating rate 10 K/min). It can be observed that this crystalline complex melts under dehydration. The obtained DSC curve is shown in FIG. 4.

Said crystalline complex of the compound A with L-proline shows a weight loss by thermal gravimetry (TG). The observed weight loss indicates that the crystalline form contains water which may be bound by adsorption and/or may be part of the crystalline lattice, i.e. the crystalline form may be present as a crystalline hydrate. The content of water in the crystalline form lies in the range from 0 to about 10 weight-%, in particular 0 to about 5 weight-%, even more preferably from about 1.5 to about 5 weight-%. The dotted line in FIG. 2 depicts a weight loss of between 2.8 and 3.8% of water. From the observed weight loss a stoichiometry close to a monohydrate can be estimated.

Said crystalline complex has advantageous physicochemical properties which are beneficial in the preparation of a pharmaceutical composition. In particular the crystalline complex has a high physical and chemical stability under various environmental conditions and during the production of a medicament. For example the crystals can be obtained in a shape and particle size which are particular suitable in a production method for solid pharmaceutical formulations. In addition the crystals show a high mechanical stability that allows grinding of the crystals. Furthermore the crystalline complex does not show a high tendency to absorb moisture and is chemically stable, i.e. the crystalline complex allows the production of a solid pharmaceutical formulation with a long shelf life. On the other hand the crystalline complex has a favorably high solubility over a wide pH-range which is advantageous in solid pharmaceutical formulations for oral administration.

The X-ray powder diffraction patterns may be recorded using a STOE—STADI P-diffractometer in transmission mode fitted with a location-sensitive detector (OED) and a Cu-anode as X-ray source (CuK$_{α1}$ radiation, λ=1.54056 Å, 40 kV, 40 mA). In Table 1 the values "2Θ[°]" denote the angle of diffraction in degrees and the values "d[Å]" denote the specified distances in Å between the lattice planes. The intensity shown in FIG. 3 is given in units of cps (counts per second).

In order to allow for experimental error, the above described 2Θ values should be considered accurate to ±0.1 degrees 2Θ, in particular ±0.05 degrees 2Θ. That is to say, when assessing whether a given sample of crystals of the compound A is the crystalline form in accordance with the above described 2Θ values, a 2Θ value which is experimentally observed for the sample should be considered identical with a characteristic value described above if it falls within ±0.1 degrees 2Θ of the characteristic value, in particular if it falls within ±0.05 degrees 2Θ of the characteristic value.

The melting point is determined by DSC (Differential Scanning calorimetry) using a DSC 821 (Mettler Toledo). The weight loss is determined by thermal gravimetry (TG) using a TGA 851 (Mettler Toledo).

Also disclosed herein is a method for making a crystalline complex as defined hereinbefore and hereinafter, said method comprising the following steps:

(a) preparing a solution of an SGLT2 inhibitor as described herein (e.g. compound A or another SGLT2 inhibitor described herein) and the one or more natural amino acids in a solvent or a mixture of solvents;

(b) storing the solution to precipitate the crystalline complex out of solution;

(c) removing the precipitate from the solution; and (d) drying the precipitate optionally until any excess of said solvent or mixture of solvents has been removed.

According to step (a) a solution of the SGLT2 inhibitor (e.g. compound A or another SGLT2 inhibitor described herein) and the one or more natural amino acids in a solvent or a mixture of solvents is prepared. Preferably the solution is saturated or at least nearly saturated or even supersaturated with respect to the crystalline complex. In the step (a) the SGLT2 inhibitor may be dissolved in a solution comprising the one or more natural amino acids or the one or more natural amino acids may be dissolved in a solution comprising the SGLT2 inhibitor. According to an alternative procedure the SGLT2 inhibitor is dissolved in a solvent or mixture of solvents to yield a first solution and the one or more natural amino acids are dissolved in a solvent or mixture of solvents to yield a second solution. Thereafter said first solution and said second solution are combined to form the solution according to step (a).

Preferably the molar ratio of the natural amino acid and the SGLT2 inhibitor (e.g. compound A or any other SGLT2 inhibitor described herein) in the solution corresponds to the molar ratio of the natural amino acid and the SGLT2 inhibitor in the crystalline complex to be obtained. Therefore a preferred molar ratio is in the range from about 1:2 to 3:1; most preferably about 1:1.

Suitable solvents are preferably selected from the group consisting of $C_{1-4}$-alkanols, water, ethylacetate, acetonitrile, acetone, diethylether, tetrahydrofuran, and mixture of two or more of these solvents.

More preferred solvents are selected from the group consisting of methanol, ethanol, isopropanol, water and mixture of two or more of these solvents, in particular mixtures of one or more of said organic solvents with water.

Particularly preferred solvents are selected from the group consisting of ethanol, isopropanol, water and mixtures of ethanol and/or isopropanol with water.

In case a mixture of water and one or more $C_{1-4}$-alkanols, in particular of methanol, ethanol and/or isopropanol, most preferably of ethanol, is taken, a preferred volume ratio of water:the alkanol is in the range from about 99:1 to 1:99; more preferably from about 50:1 to 1:80; even more preferably from about 10:1 to 1:60.

Preferably the step (a) is carried out at about room temperature (about 20° C.) or at an elevated temperature up to about the boiling point of the solvent or mixture of solvents used.

According to a preferred embodiment the starting material of the SGLT2 inhibitor (e.g. compound A or any other SGLT2 inhibitor described herein) and/or of the one or more natural amino acids and/or of the solvent and mixtures of solvents contain an amount of $H_2O$ which is at least the quantity required to form a hydrate of the SGLT2 inhibitor; in particular at least 1 mol, preferably at least 1.5 mol of water per mol of SGLT2 inhibitor. Even more preferably the amount of water is at least 2 mol of water per mol of SGLT2 inhibitor. This means that either the SGLT2 inhibitor (e.g. compound A) as starting material or the one or more natural amino acids or said solvent or mixture of solvents, or said compounds and/or solvents in combination contain an amount of $H_2O$ as specified above. For example if the starting material of the SGLT2 inhibitor (e.g. compound A) or of the natural amino acid in step (a) does contain sufficient water as specified above, a water content of the solvent(s) is not mandatory.

In order to reduce the solubility of the crystalline complex according to this invention in the solution, in step (a) and/or in step (b) one or more antisolvents may be added, preferably during step (a) or at the beginning of step (b). Water is an example of a suitable antisolvent. The amount of antisolvent is preferably chosen to obtain a supersaturated or saturated solution with respect to the crystalline complex.

In step (b) the solution is stored for a time sufficient to obtain a precipitate, i.e. the crystalline complex. The temperature of the solution in step (b) is about the same as in or lower than in step (a). During storage the temperature of the solution is preferably lowered, preferably to a temperature in the range of 20° C. to 0° C. or even lower. The step (b) can be carried out with or without stirring. As known to the one skilled in the art by the period of time and the difference of temperature in step (b) the size, shape and quality of the obtained crystals can be controlled. Furthermore the crystallization may be induced by methods as known in the art, for example by mechanical means such as scratching or rubbing the contact surface of the reaction vessel for example with a glass rod. Optionally the (nearly) saturated or supersaturated solution may be inoculated with seed crystals.

In step (c) the solvent(s) can be removed from the precipitate by known methods as for example filtration, suction filtration, decantation or centrifugation.

In step (d) an excess of the solvent(s) is removed from the precipitate by methods known to the one skilled in the art as for example by reducing the partial pressure of the solvent(s), preferably in vacuum, and/or by heating above ca. 20° C., preferably in a temperature range below 100° C., even more preferably below 85° C.

Compound A may be synthesized by methods as specifically and/or generally described or cited in international application WO 2007/128749 which in its entirety is incorporated herein by reference, and/or in the Examples disclosed herein below. Biological properties of the compound A may also be investigated as is described in WO 2007/128749.

A crystalline complex as described herein is preferably employed as drug active substance in substantially pure form, that is to say, essentially free of other crystalline forms of the SGLT2 inhibitor (e.g. compound A). Nevertheless, the invention also embraces a crystalline complex in admixture with another crystalline form or forms. Should the drug active substance be a mixture of crystalline forms, it is preferred that the substance comprises at least 50%-weight, even more preferably at least 90%-weight, most preferably at least 95%-weight of the crystalline complex as described herein.

In view of its ability to inhibit SGLT activity, a crystalline complex according to the invention is suitable for the use in the treatment and/or preventive treatment of conditions or diseases which may be affected by the inhibition of SGLT activity, particularly SGLT-2 activity, in particular the metabolic disorders as described herein. The crystalline complex according to the invention is also suitable for the preparation of pharmaceutical compositions for the treatment and/or preventive treatment of conditions or diseases which may be affected by the inhibition of SGLT activity, particularly SGLT-2 activity, in particular metabolic disorders as described herein. A crystalline complex as described herein (in particular of compound A with a natural amino acid, e.g. proline, particularly L-proline) is also suitable for the use in the treatment of canines.

Pharmaceutical Compositions and Formulations

The one or more SGLTS inhibitors, preferably compound A, for use according to the invention may be prepared as pharmaceutical compositions. It may be prepared as solid or as liquid formulations. In either case, it is preferably prepared for oral administration, preferably in liquid form for oral administration. The one or more SGLTS inhibitors, preferably compound A, may, however, also be prepared, e.g., for parenteral administration.

Solid formulations include tablets, granular forms, and other solid forms such as suppositories. Among solid formulations, tablets and granular forms are preferred.

Pharmaceutical compositions within the meaning of the present invention may comprise one or more SGLT2 inhibitors, preferably compound A, according to the present invention and one or more excipients. Any excipient that allows for, or supports, the intended medical effect may be used. Such excipients are available to the skilled person. Useful excipients are for example antiadherents (used to reduce the adhesion between the powder (granules) and the punch faces and thus prevent sticking to tablet punches), binders (solution binders or dry binders that hold the ingredients together), coatings (to protect tablet ingredients from deterioration by moisture in the air and make large or unpleasant-tasting tablets easier to swallow), disintegrants (to allow the tablet to break upon dilution), fillers, diluents, flavours, colours, glidants (flow regulators—to promote powder flow by reducing interparticle friction and cohesion), lubricants (to prevent ingredients from clumping together and from sticking to the tablet punches or capsule filling machine), preservatives, sorbents, sweeteners etc.

Formulations according to the invention, e.g. solid formulations, may comprise carriers and/or disintegrants selected from the group of sugars and sugar alcohols, e.g. mannitol, lactose, starch, cellulose, microcrystalline cellulose and cellulose derivatives, e.g. methylcellulose, and the like.

Manufacturing procedures for formulations suitable for canine animals are known to the person skilled in the art, and for solid formulations comprise, e.g., direct compression, dry granulation and wet granulation. In the direct compression process, the active ingredient and all other excipients are placed together in a compression apparatus that is directly applied to press tablets out of this material. The resulting tablets can optionally be coated afterwards in order to protect them physically and/or chemically, e.g. by a material known from the state of the art.

A unit for administration, e.g. a single liquid dose or a unit of a solid formulation, e.g. a tablet, may comprise 0.01 mg to 10 mg, or e.g. 0.3 mg to 1 mg, 1 mg to 3 mg, 3 mg to 10 mg; or 5 to 2500 mg, or e.g. 5 to 2000 mg, 5 mg to 1500 mg, 10 mg to 1500 mg, 10 mg to 1000 mg, or 10-500 mg of an SGLT2 inhibitor for use according to the invention. As the skilled person would understand, the content of the SGLT2 inhibitor in a solid formulation, or any formulation as disclosed herein for administration to a canine animal, may be increased or decreased as appropriate in proportion to the body weight of the canine animal to be treated.

In one embodiment a pharmaceutical composition for use according to the invention is designed for oral or parenteral administration, preferably for oral administration. Especially the oral administration is ameliorated by excipients which modify the smell and/or haptic properties of the pharmaceutical composition for the intended patient, e.g. as described.

When the SGLT2 inhibitor for use according to the invention is formulated for oral administration, it is preferred that excipients confer properties, e.g. palatability and/or chewability that render the formulation suitable for administration to a canine animal.

Also preferred are liquid formulations. Liquid formulations may be, e.g., solutions, syrups or suspensions. They may be administered directly to the canine animal or may be mixed with the food and/or drink (e.g. drinking water, or the like) of the canine animal One advantage of a liquid formulation (similar to a formulation in granular form), is that such a dosage form allows precise dosing. For example, the SGLT2 inhibitor may be dosed precisely in proportion to the body weight of a canine animal Typical compositions of liquid formulations are known to the person skilled in the art.

Dosing and Administration

A practitioner skilled in the art can determine suitable doses for the uses of the present invention. Preferred units dosing units include mg/kg, i.e. mg SGLT2 inhibitor per body weight of the canine animal. An SGLT2 inhibitor of the invention may, e.g., be administered in doses of 0.01-5.0 mg/kg body weight per day, e.g. 0.01-4.0 mg/kg body weight per day, e.g. 0.01-3.0 mg/kg body weight per day, e.g. 0.01-2.0 mg/kg body weight per day, e.g. 0.01-1.5 mg/kg body weight per day, e.g., 0.01-1.0 mg/kg body weight per day, e.g. 0.01-0.75 mg/kg body weight per day, e.g. 0.01-0.5 mg/kg body weight per day, e.g. 0.01-0.4 mg/kg body weight per day, e.g. 0.01-0.3 mg/kg body weight per day; or 0.1 to 3.0 mg/kg body weight per day, preferably from 0.2 to 2.0 mg/kg body weight per day, more preferably from 0.1 to 1 mg/kg body weight per day. In another preferred embodiment the dose is 0.02-0.5 mg/kg body weight per day, more preferably 0.03-0.4 mg/kg body weight per day, e.g. 0.03-0.3 mg/kg body weight per day.

A practitioner skilled in the art is able to prepare an SGLT2 inhibitor of the invention for administration according to a desired dose.

Preferably, according to the invention, an SGLT2 inhibitor is administered no more than three times per day, more preferably no more than twice per day, most preferably only once per day. The frequency of administration can be adapted to the typical feeding rate of the canine animal.

According to the invention, an SGLT2 inhibitor may be administered such that an appropriate blood plasma concentration of the SGLT2 inhibitors is achieved (e.g. a maximal blood plasma concentration, or blood plasma concentration after a given time, e.g. 4, 8, 12 or 24 hours after oral administration, preferably about 8 hours after oral administration). E.g., for compound A, the blood plasma concentration (e.g. maximal blood plasma concentration or blood plasma concentration after said given time after oral administration) may be within the range 2 to 4000 nM, e.g. 20 to 3000 nM, or e.g. 40 to 2000 nM.

Preferably, following administration and the time required for an SGLT2 inhibitor to reach the bloodstream, such levels are maintained in the blood over a time interval of at least 12 hours, more preferably at least 18 hours, most preferably at least 24 h.

Preferably, according to the invention, an SGLT2 inhibitor is administered orally, in liquid or solid form. The SGLT2 inhibitor may be administered directly to the animals mouth (e.g. using a syringe, preferably a body-weight-graduated syringe) or together with the animal's food or drink (e.g. with its drinking water or the like), in each case preferably in liquid form. The SGLT2 inhibitor may, however, also be administered, e.g., parenterally, or by any other route of administration, e.g., rectally.

The SGLT2 inhibitor may be used alone or in combination with another drug. In some embodiments, the one or more SGLTS inhibitors, preferably compound A, is used in combination with one or more further oral antihyperglycaemic drugs. When the SGLT2 inhibitor is used in combination with a further drug, the SGLT2 inhibitor and any further drug may be administered simultaneously, sequentially (in any order), and/or according to a chronologically staggered dosage regime. In such embodiments, when a further drug for combined administration with an SGLT2 inhibitor or is not administered simultaneously with an SGLT2 inhibitor, the SGLT2 inhibitor and any further drug are preferably administered within a period of at least 2 weeks, 1 month, 2 months, 4 months, 6 months or longer, e.g. 12 months or more.

In some embodiments the one or more SGLTS inhibitors, preferably compound A, is used with co-administration with insulin, preferably a simultaneous, a sequential and/or a chronologically staggered co-administration with insulin. Such co-administration can also be in the form of a fixed-dose combination (FDC), e.g. a formulation including the one or more SGLTS inhibitors, preferably compound A, and insulin combined in a single dosage form, which is manufactured and distributed in certain respective fixed doses. In some embodiments the SGLT2 inhibitor (whether used alone or in combination with another drug) is not used in combination with 1-[(3-cyano-pyridin-2-yl)methyl]-3-methyl-7-(2-butyn-1-yl)-8-[3-(R)-amino-piperidin-1-yl]-xanthine or a pharmaceutically acceptable salt thereof, i.e. the canine animal is not treated with said compound. In some embodiments the SGLT2 inhibitor is not used in combination with a DPP-IV inhibitor, i.e., the canine animal is not treated with a DPP-IV inhibitor.

In some embodiments, the SGLT2 inhibitor is used as a monotherapy, i.e. stand-alone therapy, i.e. no other medication is administered to the canine animal for the treatment or prevention of the same metabolic disorder, i.e. the metabolic disorder for which the SGLT2 inhibitor is administered. E.g., no other medication is administered to the canine animal for the treatment or prevention of the same metabolic disorder within a period of at least 2, 3, or 4 weeks before and after administration of the SGLT2 inhibitor.

EXAMPLES

Figure 1:
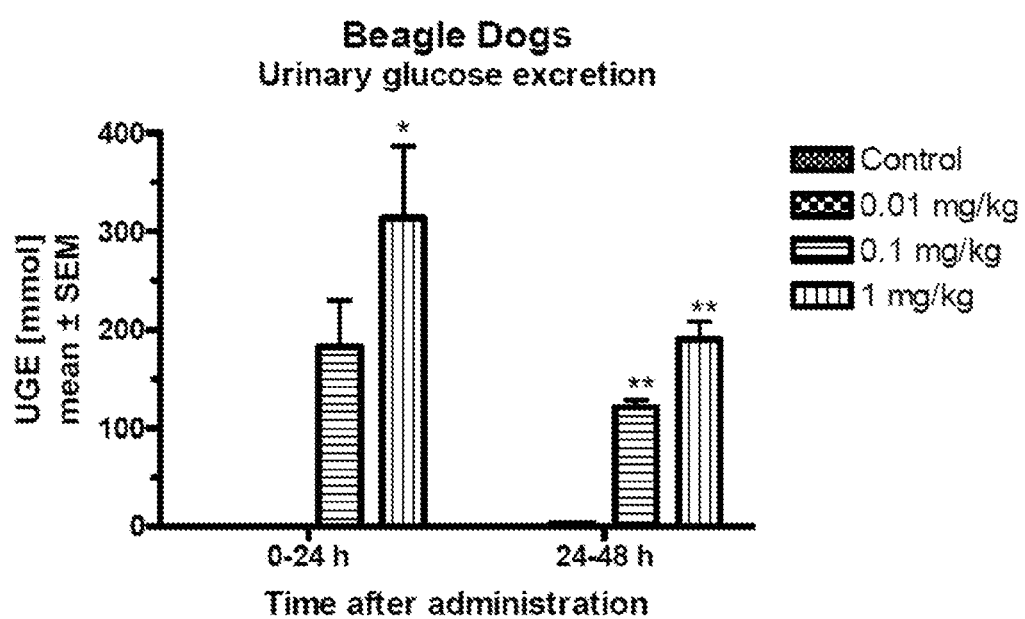
FIG. 1 Urinary glucose excretion in Beagle dogs after single oral dosing of Compound A. The urine was individually sampled 0-24 h and 24-48 h after administration. After 24 h, urine obtained by insertion of a catheter into the bladder was added to the freely sampled urine. In controls and the low dose (0.01 mg/kg) virtually no glucose was detectable in urine. Indicated p-values above bars are versus control (*, p<0.05).

The following examples show the beneficial therapeutic effects on glycaemic control and/or insulin resistance, etc., of using one or more SGLT2 inhibitors in canine animals, according to the present invention. These examples are intended to illustrate the invention in more detail without any limitation of the scope of the claims.

Example 1

Pharmacokinetics (PK) of Compound A Single Oral Dosing in Dogs

Compound A was administered to overnight fasted dogs. The groups (n=4 per group) received a single administration of either oral vehicle (DI water) containing the SGLT2 inhibitor Compound A at a dose of 1 mg/kg and 10 mg/kg or intravenous vehicle (saline) containing the SGLT2 inhibitor Compound A at a dose of 1 mg/kg. PK measurements were taken until day 3 after a single administration of compound A or its vehicle.

TABLE 2

Pharmacokinetic data, single dose
(i.v. 1 mg/kg, oral 1 and 10 mg/kg)

| Parameter | | i.v. 1 mg/kg | p.o. 1 mg/kg | p.o. 10 mg/kg |
|---|---|---|---|---|
| $t_{max}$ [hour] | mean | | 1.9 | 0.6 |
| $C_{max}$ [nmol/L] | mean | | 4845 | 51525 |
| CL [mL/min/kg] | mean | 0.63 | | |

TABLE 2-continued

Pharmacokinetic data, single dose
(i.v. 1 mg/kg, oral 1 and 10 mg/kg)

| Parameter | | i.v. 1 mg/kg | p.o. 1 mg/kg | p.o. 10 mg/kg |
|---|---|---|---|---|
| CL/F [mL/min/kg] | mean | | 0.64 | 0.71 |
| F [%] | mean | | 101 | 92 |
| $AUC_{0\to\infty}$ [nmol · h/l] | mean | 67025 | 67675 | 616750 |
| $T_{1/2}$ [hour] | mean | 13.4 | 13.9 | 14.5 |

Example 2

The Effect of Compound A on Urinary and Blood Glucose After Single Dosing in Dogs Beagle dogs were fasted overnight and received a single oral administration of Compound A at doses of 0 mg/kg b.w., 0.01 mg/kg b.w., 0.1 mg/kg b.w., or 1 mg/kg b.w. (n=3 per group) followed by a rinsing with water (1 mL/kg b.w.)

Compound A was moistened with a small volume of a 1% (w/v) aqueous Polysorbat 80 (Tween80, Polyoxyethylene Sorbitan Monooleate, ICN Biomedicals) solution and then dissolved by slowly adding a large volume of a 0.5% (w/v) aqueous hydroxyethylcellulose (Natrosol 250 HX, Boehringer Ingelheim) solution and stirring at room temperature for about 15 minutes. The final concentration of Polysorbat 80 was 0.015%. Compound A was applied in a volume of 2 mL/kg. b.w.

The animals were kept individually in metabolic cages and received food 2 h after administration. They had free access to water during the experiment. Urine was collected in the time intervals 0-8 h, 8-24 h, 24-32 h, and 32-48 h after administration. A catheter (Eickemeyer) was inserted into the bladder to completely collect the 24 h urine. This urine was combined with the urine that had been excreted in the 8-24 h period. A volume of 5 mL of a 10% solution of sodium azide in saline had been added to each urine collection tube before sampling. Volume of urine was determined and samples were frozen for subsequent determination of glucose concentration.

During the experiment, blood samples were drawn from a forearm vein. Blood was collected in EDTA tubes prior to administration of vehicle or Compound A, and subsequently at 0.25 h, 0.5 h, 1 h, 2 h, 4 h, 8 h, 24 h, 32 h, and 48 h time points post-dose. Plasma was prepared following blood collection and frozen for determination of glucose concentration.

A prominent increase of urinary glucose concentration and volume was evident at the two higher doses already 8 h after administration (FIG. 1).

Neither dose of compound A induced hypoglycemia, or altered the blood glucose level in dogs as compared to normal reference values.

Figure 2:
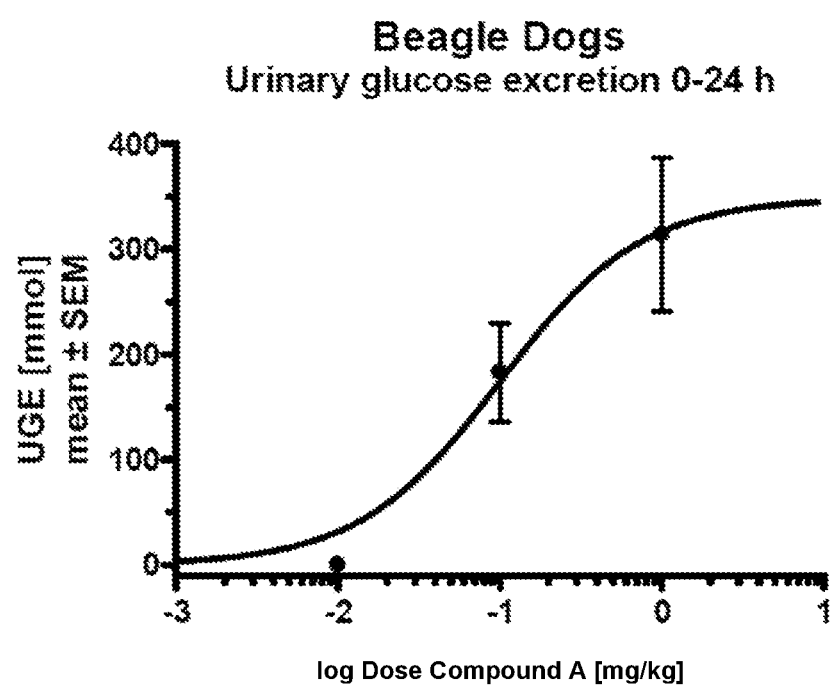
FIG. 2 Sigmoidal dose response for the urinary glucose excretion in the time period 0-24 h after administration of Compound A as shown. ED50 for glucose excretion by Compound A in Beagle dogs is 0.1 mg/kg (95% CI 0.02-0.52 mg/kg).
Figure 3:
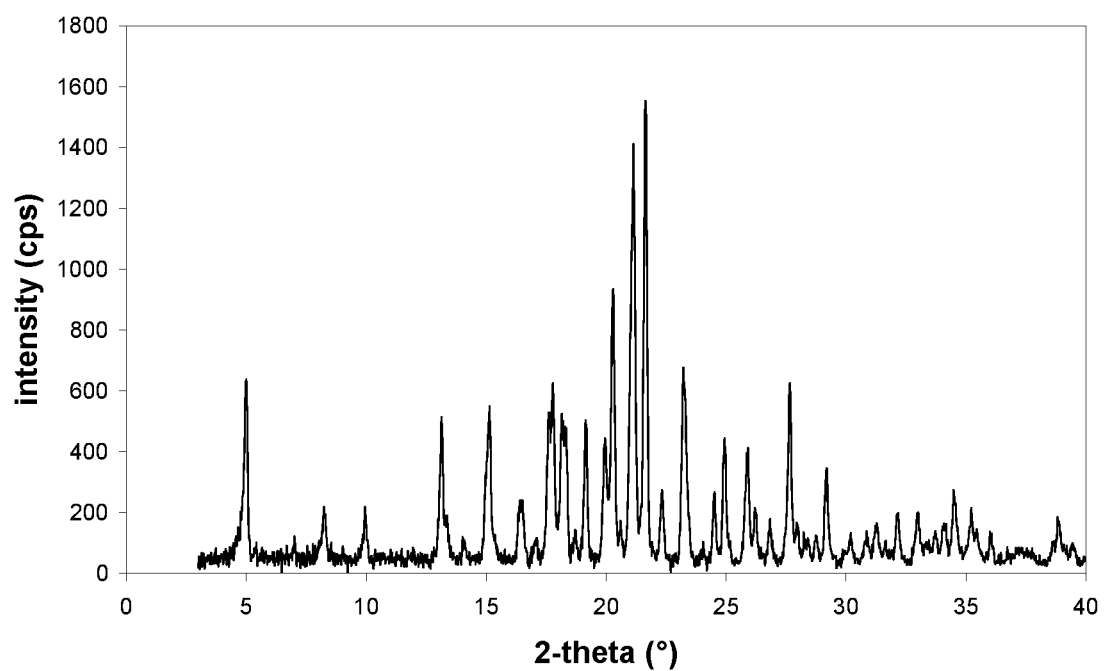
FIG. 3 shows an X-ray powder diffraction pattern of a representative batch of a crystalline complex of compound A with L-proline (1:1)
Figure 4:
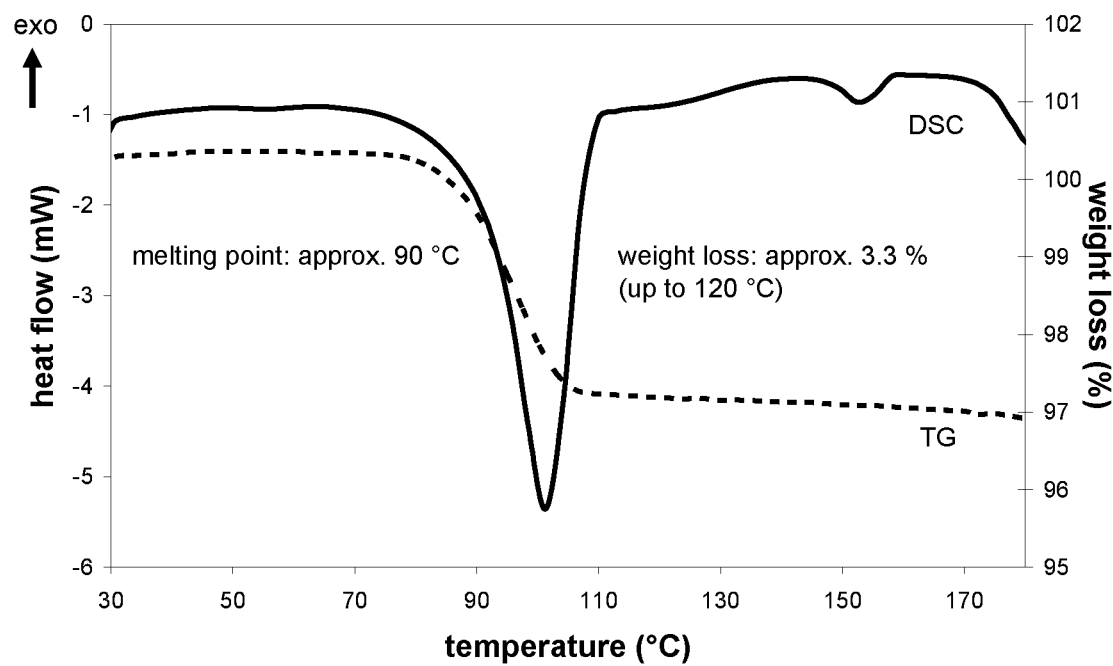
FIG. 4 shows a DSC/TG diagram of a representative batch of a crystalline complex of compound A with L-proline (1:1)

In respect to urinary glucose excretion it is thus estimated that the $ED_{50}$ is 0.1 mg/kg (FIG. 2).

Example 3

Treatment of Insulin Dependent Diabetes in Dogs

Treating Dogs With Insulin Dependent Diabetes

Insulin with the Compound A according to the invention or a combination of active substances according to the invention, in addition to producing an acute improvement in the glucose metabolic situation, prevents deterioration in the metabolic situation in the long term and reduces the insulin dose needed to treat the diabetic canine. This can be observed if dogs are treated for a shorter or longer period, e.g. 2-4 weeks or 3 months to 1 year, with the pharmaceutical composition according to the invention and are compared to the metabolic situation prior to treatment or with dogs that have been treated with e.g. insulin alone. There is evidence of therapeutic success if daily mean blood glucose and fructosamine level are reduced as compared to pre-treatment level. Further evidence of therapeutic success is obtained if a significantly smaller percentage of the dogs treated with a pharmaceutical composition according to the invention, compared with dogs who have been treated with other medications, undergo transient deterioration in the glucose metabolic position (e.g. hyper- or hypoglycaemia).

Example 4

Improvement of Insulin Resistance Diabetes in Female Dogs With Dioestrus/Gestational Diabetes Insulin resistance diabetes is a frequently found form of diabetes in intact female canine animals. Therapy with Compound A may be provided with the objective of preventing the transition to manifest diabetes. In studies over a shorter or longer period (e.g. 2-4 weeks or 1-2 years) the success of the treatment is examined by determining the fasting glucose values and/or the glucose values after a meal or after a loading test (intravenous glucose tolerance test or food tolerance test after a defined meal) during the study throughout the different phases of the menstrual cycle and/or after the end of the period of therapy for the study and comparing them with the values before the start of the study and/or with those of a placebo group. In addition, the fructosamine value can be determined before and after therapy and compared with the initial value and/or compared with dogs that have been treated with other medications or placebo. A significant drop in the fasting or non-fasting glucose and/or fructosamine levels demonstrates the efficacy of the treatment of insulin resistance—diabetes and preventing manifest diabetes in female dogs with a history of dioestrus/gestational diabetes.

Example 5

Treatment of Hyperglycaemia

In clinical studies in dogs with metabolic disorders running for different lengths of time (e.g. 2 weeks to 12 months) the success of the treatment is checked using the measurement of baseline blood glucose and/or blood fructosamine.

The improvement of glycaemic control can furthermore be determined establishing diurnal blood glucose curves, e.g. a 9 or 24 hour blood glucose curve starting prior to medication and repeated measurements post dosing.

A significant fall in these values during or at the end of the study, compared with the initial value or compared with a placebo group, or a group given a different therapy, proves the efficacy of a pharmaceutical composition according to the invention in the reduction of hyperglycaemia in dogs.

Alternatively, the effect of compound A on hyperglycaemia can be shown in dogs subject to a continuous glucose infusion (hyperglycaemic clamp). The normalization of the hyperglycaemia can be evaluated as compared to no treatment and/or to a combined treatment with insulin and/or a treatment with insulin alone.

Example 6

Prevention or Treatment of Hyperglycaemia Associated Complications

The treatment of hyperglycaemic or insulin dependent or insulin resistance diabetic dogs with Compound A according to the invention or a combination of active substances according to the invention prevents or reduces hyperglycaemia associated complications, e.g. cataract formation.

Evidence of the therapeutic success is compared with dogs that have been treated with other antidiabetic medicaments or with placebo. The success of the treatment is determined e.g. by ophthalmological eye examination of the development or the progression or the regression of cataract formation. And/or the time to development of a cataract and/or progression of the cataract maturation may be determined and be compared to dogs who have been treated with other antidiabetic medicaments or with placebo.

Example 7

Treatment of Insulin Resistance

In clinical studies in insulin resistant dogs running for different lengths of time (e.g. 4 weeks to 12 months) the success of the treatment is checked using the measurement of baseline blood glucose, blood fructosamine and blood insulin and/or c-peptide level and the corresponding relation between the parameter in the individual dog.

Also the glucose and blood lipids (e.g. NEFA) and/or insulin values after a meal or after a loading test (glucose tolerance test or insulin tolerance test) during or after the end of the period of therapy for the study can be compared with the values before the start of the study and/or with those of insulin resistant dogs who have been treated with other medications or placebo.

Example 8

Treatment of Pre-Diabetes in Dogs

The efficacy of SGLT2 inhibition in accordance with the invention in the treatment of pre-diabetes characterised by pathological fasting glucose and/or impaired glucose tolerance and/or insulin resistance can be tested using clinical studies. In studies over a shorter or longer period (e.g. 2-4 weeks or 1-2 years) the success of the treatment is examined by determining the fasting glucose values and/or the glucose values after a meal or after a loading test (intravenous glucose tolerance test or food tolerance test after a defined meal or insulin tolerance test) after the end of the period of therapy for the study and comparing them with the values before the start of the study and/or with those of a placebo group. In addition, the fructosamine value can be determined before and after therapy and compared with the initial value and/or the placebo value. A significant drop in the fasting or non-fasting glucose and/or fructosamine levels demonstrates the efficacy of the treatment of pre-diabetes Example 9

Effects on Body Weight, Body Composition, Dyslipidemia and Dysadipokinemia

Treating dogs with metabolic disorders such as obesity, dyslipidaemia, dysadipokinemia, hepatic lipidosis, subclinical inflammation or systemic inflammation, in particular low grade systemic inflammation, which also comprises adipose tissue, and associated disorders, such as Syndrome X (metabolic syndrome), and/or insulin resistance, hyperglycaemia, hyperinsulinaemia, impaired glucose tolerance is also in pursuit of the goal of preventing the transition or slowing the progression to e.g. clinically manifest consequences of the metabolic disorders e.g. hypertension, cardiomyopathy, renal dysfunction and/or musculoskeletal disorders in canine animals.

The efficacy of a treatment can be investigated in a comparative clinical study in which dogs are treated over a lengthy period (e.g. 3-12 months) with either Compound A or a combination of active substances or with placebo or with a non-drug therapy (e.g. diet) or other medicaments. Prior, during and at the end of the therapy the parameter can be determined: body weight (scale) and body composition e.g. with dual-energy x-ray absorptiometry. In plasma or serum lipid (e.g. Triglycerides, Cholesterol, NEFA) and adipokine (e.g. adiponectin, leptin) profiles as well as inflammatory markers (e.g. c-reactive protein, monocyte chemoattractant protein-I) can be measured. Insulin and glucose level can be determined basal as well as e.g. after a loading test. Renal parameter can be determined in blood and urinary samples (e.g. urea, creatinine, urinary albumin). Additionally, the blood pressure and/or also evidences of cardiomyopathy can be investigated with echocardiographic doppler ultrasound measurements. An improvement in musculoskeletal disorders (e.g. osteoarthritis) can be quantified e.g. with activity, lameness, and pain scores.

Example 10

Preparation of 1-cyano-2-(4-cyclopropyl-benzyl)-4-(β-D-glucopyranos-1-yl)-benzene (compound A)

The following example of synthesis serves to illustrate a method of preparing 1-cyano-2-(4-cyclopropyl-benzyl)-4-(β-D-glucopyranos-1-yl)-benzene (compound A). A method of preparing its crystalline complex with L-proline is also described. It is to be regarded only as a possible method described by way of example, without restriction of the scope of the invention. The terms "room temperature" and "ambient temperature" are used interchangeably and denote temperatures of about 20° C. The following abbreviations are used:
DMF dimethylformamide
NMP N-methyl-2-pyrrolidone
THF tetrahydrofuran Preparation of 4-bromo-3-hydroxymethyl-1-iodo-benzene

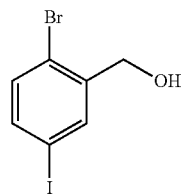

Oxalyl chloride (13.0 mL) is added to an ice-cold solution of 2-bromo-5-iodo-benzoic acid (49.5 g) in CH$_2$Cl$_2$ (200 mL). DMF (0.2 mL) is added and the solution is stirred at room temperature for 6 h. Then, the solution is concentrated under reduced pressure and the residue is dissolved in THF (100 mL). The resulting solution is cooled in an ice-bath and LiBH$_4$ (3.4 g) is added in portions. The cooling bath is removed and the mixture is stirred at room temperature for 1 h. The reaction mixture is diluted with THF and treated with 0.1 M hydrochloric acid. Then, the organic layer is separated and the aqueous layer is extracted with ethyl acetate. The combined organic layers are dried (Na$_2$SO$_4$) and the solvent is evaporated under reduced pressure to give the crude product.

Yield: 47.0 g (99% of theory)

Preparation of 4-bromo-3-chloromethyl-1-iodo-benzene

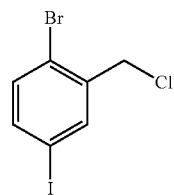

Thionyl chloride (13 mL) is added to a suspension of 4-bromo-3-hydroxymethyl-1-iodo-benzene (47.0 g) in dichloromethane (100 mL) containing DMF (0.1 mL). The mixture is stirred at ambient temperature for 3 h. Then, the solvent and the excess reagent is removed under reduced pressure. The residue is triturated with methanol and dried.

Yield: 41.0 g (82% of theory)

Preparation of 4-bromo-1-iodo-3-phenoxymethyl-benzene

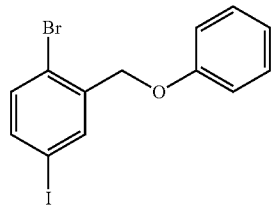 [SMILES: Brc1ccc(I)cc1COc1ccccc1]

Phenol (13 g) dissolved in 4 M KOH solution (60 mL) is added to 4-bromo-3-chloromethyl-1-iodo-benzene (41.0 g) dissolved in acetone (50 mL). NaI (0.5 g) is added and the resulting mixture is stirred at 50° C. overnight. Then, water is added and the resulting mixture is extracted with ethyl acetate. The combined extracts are dried (Na$_2$SO$_4$) and the solvent is evaporated under reduced pressure. The residue is purified by chromatography on silica gel (cyclohexane/ethyl acetate 19:1).

Yield: 38.0 g (79% of theory)

Preparation of 1-bromo-4-(1-methoxy-D-glueopyranos-1-yl)-2-(phenoxymethyl)-benzene

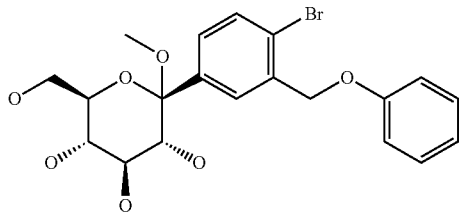 [SMILES: CO[C@@]1(c2ccc(Br)c(COc3ccccc3)c2)O[C@H](CO)[C@@H](O)[C@H](O)[C@H]1O]

A 2 M solution of iPrMgCl in THF (11 mL) is added to dry LiCl (0.47 g) suspended in THF (11 mL). The mixture is stirred at room temperature until all the LiCl is dissolved. This solution is added dropwise to a solution of 4-bromo-1-iodo-3-phenoxymethyl-benzene (8.0 g) in tetrahydrofuran (40 mL) cooled to −60° C. under argon atmosphere. The solution is warmed to −40° C. and then 2,3,4,6-tetrakis-O-(trimethylsilyl)-D-glucopyranone (10.7 g, 90% pure) in tetrahydrofuran (5 mL) is added. The resulting solution is warmed to −5° C. in the cooling bath and stirred for another 30 min at this temperature. Aqueous NH$_4$Cl solution is added and the resultant mixture is extracted with ethyl acetate. The combined organic extracts are dried over sodium sulfate and the solvent is removed under reduced pressure. The residue is dissolved in methanol (80 mL) and treated with methanesulfonic acid (0.6 mL) to produce the more stable anomer solely. After stirring the reaction solution at 35-40° C. overnight, the solution is neutralized with solid NaHCO$_3$ and the methanol is removed under reduced pressure. The remainder is diluted with aqueous NaHCO$_3$ solution and the resulting mixture is extracted with ethyl acetate. The combined extracts are dried over sodium sulfate and the solvent is evaporated to yield the crude product that is submitted to reduction without further purification.

Yield: 7.8 g (93% of theory)

Preparation of 1-bromo-4-(2,3,4,6-tetra-O-acetyl-D-glueopyranos-1-yl)-2-(phenoxymethyl)-benzene

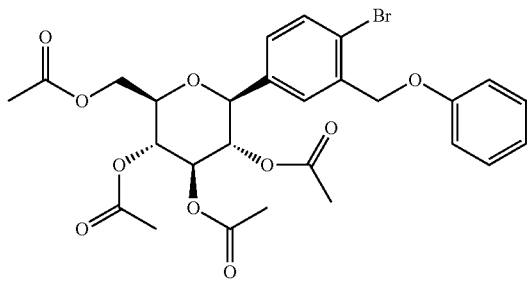 [SMILES: CC(=O)OC[C@H]1O[C@@H](c2ccc(Br)c(COc3ccccc3)c2)[C@H](OC(C)=O)[C@@H](OC(C)=O)[C@@H]1OC(C)=O]

Boron trifluoride diethyletherate (4.9 mL) is added to a solution of 1-bromo-4-(1-methoxy-D-glucopyranos-1-yl)-2-(phenoxymethyl)-benzene (8.7 g) and triethylsilane (9.1 mL) in dichloromethane (35 mL) and acetonitrile (50 mL) cooled to −20° C. at such a rate that the temperature maintains below −10° C. The resultant solution is warmed to 0° C. over a period of 1.5 h and then treated with aqueous sodium hydrogen carbonate solution. The resulting mixture is stirred for 0.5 h, the organic solvent is removed and the residue is extracted with ethyl acetate. The combined organic layers are dried over sodium sulfate and the solvent is removed. The residue is taken up in dichloromethane (50 mL) and pyridine (9.4 mL), acetic anhydride (9.3 mL) and 4-dimethylaminopyridine (0.5 g) are added in succession to the solution. The solution is stirred for 1.5 h at ambient temperature and then diluted with dichloromethane. This solution is washed twice with 1 M hydrochloric acid and dried over sodium sulfate. After the solvent is removed, the residue is recrystallized from ethanol to furnish the product as a colourless solid.

Yield: 6.78 g (60% of theory)

Mass spectrum (ESI$^+$): m/z=610/612 (Br) [M+NH$_4$]$^+$

Preparation of 2-(phenoxymethyl)-4-(2,3,4,6-tetra-O-acetyl-D-glueopyranos-1-yl)-benzonitrile

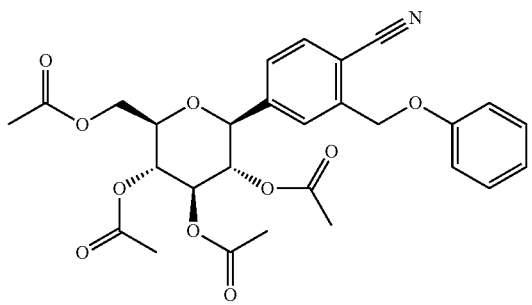 [SMILES: CC(=O)OC[C@H]1O[C@@H](c2ccc(C#N)c(COc3ccccc3)c2)[C@H](OC(C)=O)[C@@H](OC(C)=O)[C@@H]1OC(C)=O]

A flask charged with zinc cyanide (1.0 g), zinc (30 mg), Pd$_2$(dibenzylideneacetone)$_3$*CHCl$_3$ (141 mg) and tri-tert-butylphosphonium tetrafluoroborate (111 mg) is flushed with argon. Then a solution of 1-bromo-4-(2,3,4,6-tetra-O-acetyl-D-glucopyranos-1-yl)-2-(phenoxymethyl)-benzene (5.4 g) in NMP (12 mL) is added and the resulting mixture is stirred at room temperature for 18 h. After dilution with ethyl acetate, the mixture is filtered and the filtrate is washed with aqueous sodium hydrogen carbonate solution. The organic phase is dried (sodium sulfate) and the solvent is removed. The residue is recrystallized from ethanol.

Yield: 4.10 g (84% of theory)

Mass spectrum (ESI$^+$): m/z=557 [M+NH$_4$]$^+$

Alternatively, the compound described above is synthesized starting from 1-bromo-4-(2,3,4,6-tetra-O-acetyl-D-glucopyranos-1-yl)-2-(phenoxymethyl)-benzene using copper(I) cyanide (2 equivalents) in NMP at 210° C.

Preparation of 2-bromomethyl-4-(2,3,4,6-tetra-O-acetyl-D-glucopyranos-1-yl)-benzonitrile

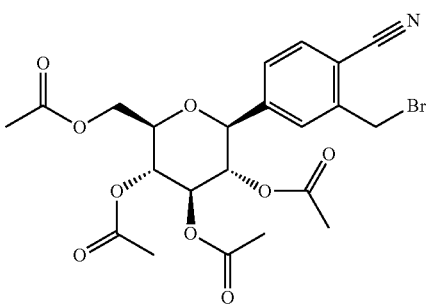 [SMILES: CC(=O)OC[C@H]1O[C@@H](c2ccc(C#N)c(CBr)c2)[C@H](OC(C)=O)[C@@H](OC(C)=O)[C@@H]1OC(C)=O]

A 33% solution of hydrobromic acid in acetic acid (15 mL) is added to a solution of 2-phenyloxymethyl-4-(2,3,4,6-tetra-O-acetyl-D-glucopyranos-1-yl)-benzonitrile (0.71 g) and acetic anhydride (0.12 mL) in acetic acid (10 ml). The resulting solution is stirred at 55° C. for 6 h and then cooled in an ice-bath. The reaction mixture is neutralized with chilled aqueous potassium carbonate solution, and the resultant mixture is extracted with ethyl acetate. The combined organic extracts are dried over sodium sulfate and the solvent is removed under reduced pressure. The residue is taken up in ethyl acetate/cyclohexane (1:5), and the precipitate is separated by filtration and dried at 50° C. to give the pure product.

Yield: 0.52 g (75% of theory)

Mass spectrum (ESI$^+$): m/z=543/545 (Br) [M+NH$_4$]$^+$

Preparation of 4-cyclopropyl-phenylboronic acid

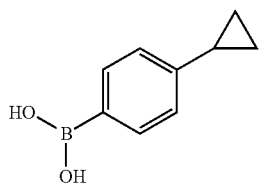 [SMILES: OB(O)c1ccc(C2CC2)cc1]

2.5 M solution of nButyllithium in hexane (14.5 mL) is added dropwise to 1-bromo-4-cyclopropyl-benzene (5.92 g) dissolved in THF (14 mL) and toluene (50 mL) and chilled to −70° C. The resultant solution is stirred at −70° C. for 30 min before triisopropyl borate (8.5 mL) is added. The solution is warmed to −20° C. and then treated with 4 M aqueous hydrochloric acid (15.5 mL). The reaction mixture is further warmed to room temperature and then the organic phase is separated. The aqueous phase is extracted with ethyl acetate and the combined organic phases are dried (sodium sulfate). The solvent is evaporated and the residue is washed with a mixture of ether and cyclohexane to give the product as a colourless solid.

Yield: 2.92 g (60% of theory)

Mass spectrum (ESI$^-$): m/z=207 (Cl) [M+HCOO]$^-$

Preparation of 1-cyano-2-(4-cyclopropyl-benzyl)-4-(β-D-glucopyranos-1-yl)-benzene

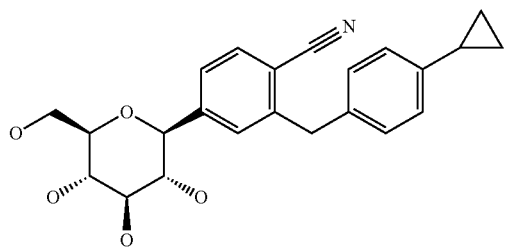 [SMILES: N#Cc1ccc([C@@H]2O[C@H](CO)[C@@H](O)[C@H](O)[C@H]2O)cc1Cc1ccc(C2CC2)cc1]

An Ar filled flask is charged with 2-bromomethyl-4-(2,3,4,6-tetra-O-acetyl-D-glucopyranos-1-yl)-benzonitrile (1.60 g), 4-cyclopropyl-phenylboronic acid (1.0 g), potassium carbonate (1.85 g) and a degassed 3:1 mixture of acetone and water (22 mL). The mixture is stirred at room temperature for 5 min, before it is cooled in an ice-bath. Then palladium dichloride (30 mg) is added and the reaction mixture is stirred for 16 h at ambient temperature. The mixture is then diluted with brine and extracted with ethyl acetate. The combined extracts are dried over sodium sulfate and the solvent is removed under reduced pressure. The residue is dissolved in methanol (20 mL) and treated with 4 M aqueous potassium hydroxide solution (4 mL). The resulting solution is stirred at ambient temperature for 1 h and then neutralized with 1 M hydrochloric acid. The methanol is evaporated, and the residue is diluted with brine and extracted with ethyl acetate. The organic extracts collected are dried over sodium sulfate, and the solvent is removed. The residue is chromatographed on silica gel (dichloromethane/methanol 1:0→8:1).

Yield: 0.91 g (76% of theory)

Mass spectrum (ESI$^+$): m/z=413 [M+NH$_4$]$^+$

Preparation of a Crystalline Complex (1:1) of Compound A With L-proline

L-proline (0.34 g) dissolved in 2.1 mL of a mixture of ethanol and water (volume ratio 10:1) is added to a solution of 1-cyano-2-(4-cyclopropyl-benzyl)-4-(β-D-glucopyranos-1-yl)-benzene (1.17 g, obtained as described above) dissolved in 2 mL ethanol. The resulting solution is allowed to stand at ambient temperature. After about 16 h the crystalline complex is isolated as white crystals by filtration. If necessary the crystallisation may be initiated by scratching with a glass rod or metal spatula for example or by inoculating with seed crystals. Residual solvent is removed by storing the crystals at slightly elevated temperature (30 to 50° C.) under vacuum for about 4 h to yield 1.27 g of the crystalline 1:1 complex of L-proline and 1-cyano-2-(4-cyclopropyl-benzyl)-4-(β-D-glucopyranos-1-yl)-benzene.

Several batches of the crystalline complex according to the above preparation are obtained. The X-ray powder diffraction patterns coincide. The melting points are determined via DSC and evaluated as onset-temperature. Examples of melting points are approximately 89° C., 90° C., 92° C., 101° C. and 110° C. The X-ray powder diffraction pattern as contained in Table 1 and as depicted in FIG. 11 and the DSC and TG diagram in FIG. 12 correspond to a batch with a melting point of approximately 90° C.

The X-ray powder diffraction pattern of the crystalline complex of the compound A and L-proline (peaks up to 30° in 2Θ) is provided above in Table 1.

Example 11

Formulations

Some examples of formulations are described in which the term "active substance" denotes an SGLT2 inhibitor or pharmaceutically acceptable form thereof, e.g. a prodrug or a crystalline form, for use according to the invention. In the case of a combination with one or additional active substances, the term "active substance" may also include the additional active substance.

Tablets Containing 100 mg of Active Substance

Composition:

1 tablet contains:

| | |
|---|---|
| active substance | 100.0 mg |
| lactose | 80.0 mg |
| corn starch | 34.0 mg |

|  |  |
|---|---:|
| polyvinylpyrrolidone | 4.0 mg |
| magnesium stearate | 2.0 mg |
|  | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Tablets Containing 150 mg of Active Substance
Composition:
1 tablet contains:

|  |  |
|---|---:|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
|  | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

Hard Gelatine Capsules Containing 150 mg of Active Substance
Composition:
1 capsule contains:

|  |  |
|---|---:|
| active substance | 150.0 mg |
| corn starch (dried) | approx. 180.0 mg |
| lactose (powdered) | approx. 87.0 mg |
| magnesium stearate | 3.0 mg |
|  | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

Suppositories containing 150 mg of active substance
Composition:
1 suppository contains:

|  |  |
|---|---:|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
|  | 2,000.0 mg |

Preparation:

After the suppository mass has been melted the active substance is homogeneously distributed therein and the melt is poured into chilled moulds.

Ampoules Containing 10 mg Active Substance
Composition:

|  |  |
|---|---:|
| active substance | 10.0 mg |
| 0.01N hydrochloric acid/NaCl | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

Ampoules Containing 50 mg of Active Substance
Composition:

|  |  |
|---|---:|
| active substance | 50.0 mg |
| 0.01N hydrochloric acid/NaCl | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

REFERENCES

1) Beam et al. Vet. Ophtalmol. 1999. 2, 169-172
2) Catchpole et al., Diabetologia 2005. 48: 1948-1956
3) EP 1 213 296
4) EP 1 354 888
5) EP 1 344 780
6) EP 1 489 089
7) Nelson et al. J small Anim Pract 2000, 41, 486-490
8) Verkest, Vet J, in press doi.org/10.1016/j.tvjl.2013.09.057
9) Wang et al. J Diabet. Compl. in press, doi:0.1016/j.jdiacomp.2013.11.002
10) WO 01/27128
11) WO 03/099836
12) WO 2004/007517
13) WO 2004/080990
14) WO 2005/012326
15) WO 2005/092877
16) WO 2006/034489
17) WO 2006/064033
18) WO 2006/117359
19) WO 2006/117360
20) WO 2006/120208
21) WO 2007/025943
22) WO 2007/028814
23) WO 2007/031548
24) WO 2007/093610
25) WO 2007/114475
26) WO 2007/128749
27) WO 2007/140191
28) WO 2008/002824

29) WO 2008/013280
30) WO 2008/042688
31) WO 2008/049923
32) WO 2008/055870
33) WO 2008/055940
34) WO 2008/069327
35) WO 2008/116179
36) WO 2009/014970
37) WO 2009/022008
38) WO 2009/022020
39) WO 2009/035969
40) WO 2010/023594
41) WO 2011/039107
42) WO 2011/039108
43) WO 2011/117295
44) WO 2014/016381

The invention claimed is:

1. A method of treatment of a metabolic disorder in a canine animal comprising administering to the canine animal a composition comprising one or more active agents, where the one or more active agents consist of one or more SGLT2 inhibitors or pharmaceutically acceptable forms thereof;

wherein:
the one or more SGLT-2 inhibitors or pharmaceutically acceptable forms thereof comprises 1-cyano-2-(4-cyclopropyl-benzyl)-4-(β-D-glucopyranos-1-yl)-benzene or a pharmaceutically acceptable form thereof represented by the following formula:

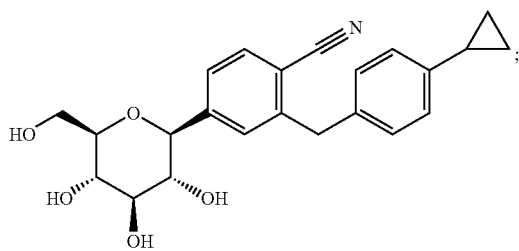 [SMILES: N#Cc1ccc([C@@H]2O[C@H](CO)[C@@H](O)[C@H](O)[C@H]2O)cc1Cc1ccc(C2CC2)cc1]

the metabolic disorder is one or more selected from the group consisting of ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences comprising hypertension, renal dysfunction and/or musculoskeletal disorders, and Syndrome X (metabolic syndrome); and the one or more SGLT-2 inhibitors or pharmaceutically acceptable forms thereof is administered at a dose of no greater than 2.0 mg/kg bodyweight.

2. The method of claim 1, wherein the development of hyperglycemia induced cataract formation is prevented or remission is achieved and/or the development of metabolic disorder consequences prevented or progression is slowed or remission is achieved.

3. The method of claim 1, wherein the metabolic disorder is selected from the group consisting of clinical conditions associated with pre-diabetes, insulin dependent diabetes mellitus and insulin resistance.

4. The method of claim 3, wherein the clinical conditions are one or more conditions selected from the group consisting of ketoacidosis, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences comprising hypertension, renal dysfunction and/or musculoskeletal disorders, and Syndrome X (metabolic syndrome).

5. The method of claim 1, wherein the canine animal is suffering from diabetes.

6. The method of claim 1, wherein the canine animal is suffering from pre-diabetes or insulin dependent diabetes.

7. The method of claim 1, wherein the canine animal is a dog.

8. The method of claim 1, wherein the pharmaceutically acceptable form thereof is a crystalline complex between the one or more SGLT-2 inhibitors and one or more amino acids.

9. The method of claim 8, wherein the one or more amino acids comprise proline.

10. The method of claim 8, wherein the one or more amino acids comprise L-proline.

11. The method of claim 1, wherein the one or more SGLT-2 inhibitors or pharmaceutically acceptable forms thereof is administered orally or parenterally.

12. The method of claim 1, wherein the one or more SGLT-2 inhibitors or pharmaceutically acceptable forms thereof is administered once per day.

13. The method of claim 1, wherein the one or more SGLT-2 inhibitors or pharmaceutically acceptable forms thereof is administered at a dose of 0.01 to 1.0 mg/kg bodyweight.

* * * * *